US012697381B2

(12) United States Patent
Van Den Born

(10) Patent No.: US 12,697,381 B2
(45) Date of Patent: Aug. 4, 2026

(54) BACULOVIRUS EXPRESSION VECTOR

(71) Applicant: Intervet Inc., Madison, NJ (US)

(72) Inventor: Erwin Van Den Born, Boxmeer (NL)

(73) Assignee: Intervet, Inc., Rahway, NJ (US)

( * ) Notice: Subject to any disclaimer, the term of this patent is extended or adjusted under 35 U.S.C. 154(b) by 573 days.

(21) Appl. No.: 18/249,431

(22) PCT Filed: Oct. 21, 2021

(86) PCT No.: PCT/EP2021/079180
§ 371 (c)(1),
(2) Date: Apr. 18, 2023

(87) PCT Pub. No.: WO2022/084438
PCT Pub. Date: Apr. 28, 2022

(65) Prior Publication Data
US 2023/0390380 A1 Dec. 7, 2023

(30) Foreign Application Priority Data

Oct. 22, 2020 (EP) .................................... 20203379

(51) Int. Cl.
*A61K 39/135* (2006.01)
*C12N 15/866* (2006.01)

(52) U.S. Cl.
CPC .......... *A61K 39/135* (2013.01); *C12N 15/866* (2013.01); *C12N 2710/14041* (2013.01); *C12N 2780/00034* (2013.01); *C12N 2799/026* (2013.01)

(58) Field of Classification Search
None
See application file for complete search history.

(56) References Cited

U.S. PATENT DOCUMENTS

2016/0052973 A1* 2/2016 Kotecha ................. A61K 39/12
435/235.1
2023/0390380 A1* 12/2023 Van Den Born .... A61K 39/135

FOREIGN PATENT DOCUMENTS

CA 1330425 C 6/1994
CN 105056227 B 12/2017
WO WO 2016049209 A1 3/2016
(Continued)

OTHER PUBLICATIONS

Porta et al. (Journal of Virological Methods. 2013; 187: 406-412).*
(Continued)

*Primary Examiner* — Shanon A. Foley
(74) *Attorney, Agent, or Firm* — Susanna C. Benn

(57) ABSTRACT

The invention concerns a baculovirus expression vector for recombinantly expressing a Foot-and-mouth disease virus (FMDV) capsid precursor protein under control of a promoter, the expression vector comprising a nucleic acid sequence encoding the FMDV capsid precursor protein, wherein the ATG start codon of an open reading frame encoding the FMDV capsid precursor protein is preceded at position −4 to −1 by the nucleic acid sequence 5'-AAAT-3'. The invention further relates to a host cell comprising the baculovirus expression vector, a method of producing FMDV virus-like particles (VLPs), and a method of producing a vaccine.

13 Claims, 2 Drawing Sheets

Figure 1:
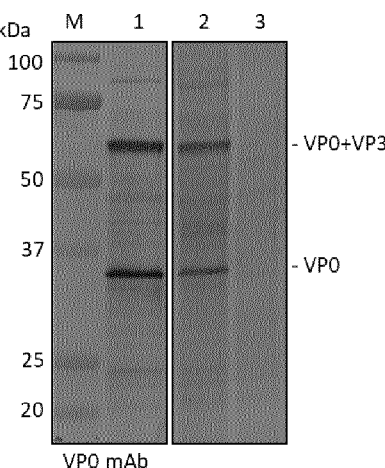

Specification includes a Sequence Listing.

VP0 mAb

M Marker BioRad Precision Plus
1. AAAT – cells (10x concentrated)
2. Standard – cells (10x concentrated)
3. Uninfected Tni cells SAT2 mAbs M Marker BioRad Precision Plus
1. AAAT – cells (10x concentrated)
2. Standard – cells (10x concentrated)
3. Uninfected Tni cells

(56)          References Cited

FOREIGN PATENT DOCUMENTS

WO          2017132666 A1      8/2017

OTHER PUBLICATIONS

Lautenberger et al. (Gene. 1980: 171-174).*

Li et al. (PLoS One. 2008; 3 (5): e2273).*

Badri, H. et al., Optimization of radiation dosing schedules for proneural glioblastoma, J Math Bio, 72(5), 1301-1336 (Abstract Only), 2016.

Baylot, Virginie et al., TCTP Has a Crucial Role in the Different Stages of Prostate Cancer Malignant Progression, Results Probl Cell Differ, 64, 255-261 (Abstract Only), 2017.

Ruiz, V. et al., Comparison of Strategies for the Production of FMDV Empty Capsids Using the Baculovirus Vector System, Mol Biotechnol, 56, 963-970, 2014.

Shaikh, Hanif et al., Current and future cholera vaccines, Vaccine, 38, A118-A126, 2020.

Li et al., 2016, "Novel chimeric foot-and-mouth disease virus-like particles harboring serotype O VP1 protect guinea pigs against challenge," Vet. Microbiol., 183:92-96 (Epub 2015).

Martinez-Solis et al., 2019, "Engineering of the baculovirus expression system for optimized protein production," Appl. Microbiol. Biotechnol., 103(1):113-123 (Epub 2018).

Subramanian et al., 2012, "Development of foot-and-mouth disease virus (FMDV) serotype O virus-like-particles (VLPs) vaccine and evaluation of its potency," Antiviral Res., 96(3):288-295.

Deepak, P.R. et al., Generation of acid resistant virus like particles of vaccine strains of foot-and mouth disease virus (FMDV), Biologicals, 60, 28-35, 2019.

Kang, C Yong, Expression of Human Immunodeficiency Virus Genes Using Baculovirus Expression System, Mol Biotechnol, 8, 173-187, 1997.

Lin, Qinying et al., Improved Heterologous Expression of the White-Rot Fungal Ligninase H8 by Crossover Linker Mutagenesis, Appl Biochemi Biotechnol, 66, 269-279, 1997.

* cited by examiner

VP0 mAb

M   Marker BioRad Precision Plus
1.   AAAT – cells (10x concentrated)
2.   Standard – cells (10x concentrated)
3.   Uninfected Tni cells SAT2 mAbs M   Marker BioRad Precision Plus
1.   AAAT – cells (10x concentrated)
2.   Standard – cells (10x concentrated)
3.   Uninfected Tni cells M   Marker BioRad Precision Plus
1.  AAAT – cells (10x concentrated)
2.  AAAT – supernatant
3.  Standard – cells (10x concentrated)
4.  Standard – supernatant M   Marker BioRad Precision Plus
1.  AAAT – cells (10x concentrated)
2.  AAAT – supernatant
3.  Standard – cells (10x concentrated)
4.  Standard – supernatant

BACULOVIRUS EXPRESSION VECTOR

SEQUENCE LISTING

The instant application contains an electronic Sequence Listing which has been submitted in txt format via the Patent Center, the entire content of which is hereby incorporated by reference in its entirety. The Sequence Listing txt file submitted via the Patent Center is entitled "25115WO-SEQL.txt" and was created on Oct. 21, 2020, and is 61,440 bytes in size.

CROSS-REFERENCE TO RELATED APPLICATIONS

This application is a National Stage application of International Patent Application No. PCT/EP2021/079180, filed Oct. 21, 2021, which claims priority to European Patent Application No. 20203379.1, filed Oct. 22, 2020.

The invention concerns a baculovirus expression vector for recombinantly expressing a Foot-and-mouth disease virus (FMDV) capsid precursor protein under control of a promoter, the expression vector comprising a nucleic acid sequence encoding the FMDV capsid precursor protein. The invention further relates to a host cell comprising the baculovirus expression vector, a method of producing FMDV virus-like particles (VLPs), and a method of producing a vaccine.

BACKGROUND OF THE INVENTION

Foot-and-mouth disease (FMD) is a highly contagious, acute viral disease of cloven-hoofed, domesticated and wild animals. It is classified as a transboundary animal disease by the Food and Agriculture Organisation of the United Nations (FAO). It is also a notifiable disease. Foot-and-mouth disease is endemic in large parts of Africa, South America, The Middle East and Asia and is, globally, the most economically important infectious disease of livestock, affecting cattle, pigs, sheep, goats and other artiodactyl species like buffalo and deer. FMD was once distributed worldwide but has been eradicated in some regions, including North America and Western Europe. In endemic countries, FMD places economic constraints on the international livestock trade and can be easily reintroduced into disease-free areas unless strict precautions are in place. FMD impacts on the whole livestock industry with loss of income for local farmers.

Current vaccines are made of inactivated virus. Before the virus is inactivated, live FMD virus is produced in high containment facilities, limiting FMD vaccine production. Effective vaccination against FMD requires the presence of intact FMDV capsids rather than the capsid building blocks that have been proven to be insufficiently immunogenic (Doel and Chong, 1982, Archives of Virology). The inactivated FMD viruses are fragile structures that at acidic pH or at elevated temperatures easily fall apart in the capsid building blocks. Hence, a cold chain is required to deliver effective FMD vaccines to livestock keepers.

A new vaccine technology for commercial FMD vaccines that can overcome many of the drawbacks of the current inactivated virus vaccines is needed.

The virus-like particle (VLP) technology is currently considered one of the few technologies with the potential to be a viable alternative to conventional inactivated vaccines. The benefits of the VLP technology as compared to the current technology are for example higher product stability, greater flexibility in production location (low-containment production), and quicker responses to outbreaks of new strains. VLP-based vaccines are typically designed as marker vaccines which relieves the necessity of implementing production steps to remove non-structural proteins.

The FMDV genome encodes a single open reading frame (ORF) that produces a precursor polyprotein that is processed into twelve mature viral proteins, FIG. 1A (from: Balinda et al. Virology Journal 2010, 7:199). The P1 polyprotein intermediate is comprised of four capsid structural proteins, VP1-VP4, sited immediately upstream of the 2A protein which causes non-proteolytic separation of the P1 and P2 polyproteins during translation to release P1-2A from P2. The P1-2A polyprotein is subsequently processed by the FMDV 3C protease into 2A, VP0 (also known as 1AB), VP3 (1C), and VP1 (1D). The VP0 protein separates into VP4 and VP2 during encapsulation. FMDV virions are formed by self-assembly from the processed virus structural proteins.

VLPs for use in VLP-based vaccines can be produced by recombinantly expressing FMDV precursor proteins in suitable host cells in analogy to the self-assembly of FMDV virions. FMDV VLP's are likewise formed by self-assembly from the processed virus structural proteins.

The thermostability and sensitivity to low pH of VLPs can be improved by the introduction of covalent links between the capsid proteins, such as cysteine bridges, or by the introduction of other rationally designed mutations (Porta et al. (2013) PLoS Pathog).

Because the initial yield of FMDV VLPs per milliliter cell culture is typically low, even when using common successful expression systems, there is a need to increase expression levels to make the VLP-based FMD vaccine a cost-effective alternative to the classic FMD vaccines currently on the market. Therefore, the baculovirus expression vector was optimized to improve the yield of VLPs and to achieve a large-scale production process that at least equals or even outperforms the conventional FMD vaccine production process in terms of antigen yield.

The baculovirus expression vector platform is currently used as one of the preferred platforms for the production of VLPs. However, the relatively low expression levels of FMDV VLPs provided by the baculovirus expression platform limits the development of a VLP-based FMD vaccine.

SUMMARY OF THE INVENTION

In the present invention, it has surprisingly been found that expression of an FMDV capsid precursor protein via the baculovirus expression system can be enhanced by optimizing the nucleic acid initiation sequence preceding the start codon of the open reading frame (ORF) encoding the FMDV capsid precursor protein. It could surprisingly be shown that in case the initiation sequence has the nucleic acid sequence at position −4 to −1 of 5'-AAAT-3', the expression yields can be enhanced compared to baculovirus expression systems used in the art.

Thus, in a first aspect the present invention provides a baculovirus expression vector capable of recombinantly expressing a Foot and mouth disease virus (FMDV) capsid precursor protein under control of a promoter, the expression vector comprising a nucleic acid sequence encoding the FMDV capsid precursor protein, wherein the ATG start codon of an open reading frame encoding the FMDV capsid precursor protein is preceded at position −4 to −1 by the nucleic acid sequence 5"-AAAT-3".

In a second aspect of the invention, there is provided a host cell comprising the baculovirus expression vector of the present invention. Such a host cell can be used in vitro, in a tissue culture, the host cell typically being an immortalized cell.

In a third aspect, the invention provides a method of producing FMDV capsid precursor proteins, the method comprising the steps of: infecting a host cell with the baculovirus expression vector as described herein, and harvesting FMDV capsid precursor proteins produced by the host cell.

The invention further provides a method of producing FMDV VLPs, the method comprising the steps of: infecting a host cell with the baculovirus expression vector as described herein, wherein the expression vector further comprises a nucleic acid sequence encoding a protease capable of cleaving a capsid precursor protein into one or more capsid proteins to assemble into VLPs, and harvesting the VLPs produced by the host cell.

The invention further relates to the use of the baculovirus expression vector for the recombinant expression of a FMDV capsid precursor protein.

The invention further relates to a method of producing a vaccine by producing FMDV VLPs and incorporating the FMDV VLPs into a vaccine by addition of a pharmaceutically acceptable carrier.

The invention further relates to a method of protecting a subject against an infection with FMDV by expressing an FMDV capsid precursor protein from the baculovirus expression vector of the present invention in a host cell to produce VLPs, incorporating the VLPs into a vaccine by addition of a pharmaceutically acceptable carrier and administering the VLPs to the subject.

The invention further relates to a baculovirus expression vector according to the first aspect of the invention for use in the protection of a subject against an infection with FMDV.

The invention further relates to a baculovirus expression vector as described herein for use in the manufacture of a medicament for the protection of a subject against an infection with FMDV.

FIG. 1 is a Western Blot using anti-VP0 monoclonal antibody showing the level of expression of the Asia1/Irn/49/2011 VP2-S93Y FMDV capsid precursor protein of Asia1 serotype in Tni cells transfected with a baculovirus expression cassette comprising the AAAT sequence (lane 1) as compared to expression levels of Tni cells transfected with a baculovirus expression cassette without the AAAT sequence (lane 2).

Figure 2:
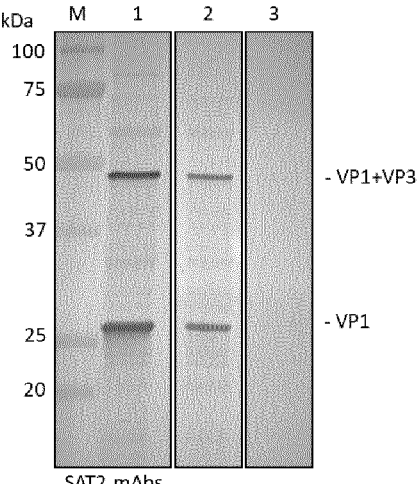

FIG. 2 is a Western Blot using a cocktail of 5 SAT2-specific monoclonal antibodies: 1D5, DA10, GE11, GD12, and GG1 showing the level of expression of the SAT2/Egy/2/12 VP2-K93Y FMDV capsid precursor protein of serotype SAT2 serotype in Tni cells after transfection with a baculovirus expression cassette comprising the AAAT sequence (lane 1), as compared to expression levels in Tni cells after transfection with a baculovirus expression cassette without the AAAT sequence (lane 2).

Figure 3:
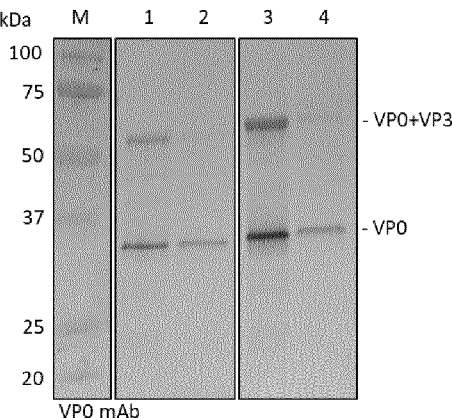

FIG. 3 is a Western Blot using an anti-VP0 monoclonal antibody showing the level of expression of the O/Tur/5/09 VP2-S93F FMDV capsid precursor protein of FMDV O serotype Tni cells (lane 1) and supernatant (lane 2) after transfection with a baculovirus expression cassette comprising the AAAT sequence, as compared to expression levels in Tni cells (lane 3) and supernatant (lane 4) after transfection with a baculovirus expression cassette without the AAAT sequence.

Figure 4:
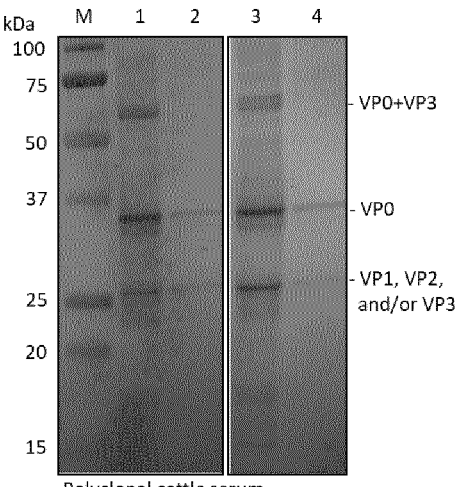

FIG. 4 is a Western Blot using polyclonal cattle serum showing the level of expression of the A/Irn/7/13 VP2-H93F FMDV capsid precursor protein of FMDV A serotype in Tni cells (lane 1) and supernatant (lane 2) after transfection with a baculovirus expression cassette comprising the AAAT sequence, as compared to expression levels in Tni cells (lane 3) and supernatant (lane 4) after transfection with a baculovirus expression cassette without the AAAT sequence.

DETAILED DESCRIPTION OF THE INVENTION

Definition of Terms

The term "nucleic acid sequence" includes an RNA or DNA sequence. It may be single or double stranded. It may, for example, be genomic, recombinant, mRNA or cDNA.

The term "initiation sequence" herein refers to the nucleic acid sequence in direct proximity upstream, i.e. in 5' direction, of the ATG start codon of an open reading frame (ORF) encoding an FMDV capsid precursor protein. In consistency with conventional nomenclature, the "A" nucleotide of this ATG start codon is enumerated as "+1". More specifically, the term "initiation sequence" in the present invention refers to the nucleic acid sequence 5 '-AAAT-3' at position −4 to −1 relative to this ATG start codon.

An "expression vector" (syn. "expression construct"), is usually a plasmid or virus designed for recombinant gene expression in cells. The vector is used to introduce a specific gene into a target cell, and can commandeer the cell's mechanism for protein synthesis to produce the protein of interest (POI) encoded by the gene. In order to express the recombinant gene to produce the POI, the expression vector typically comprises at least a promotor for initiating gene expression and may further comprise one or more translational enhancers.

A "baculovirus expression vector" is an expression vector based on a baculovirus, which is used for recombinant gene expression in a host cell, such as an insect cell. Baculovirus expression systems are established in the art and are commercially available, such as the Bac-to-Bac expression system (ThermoFisher Scientific, Germany). In these baculovirus expression systems, the naturally occurring polyhedrin gene within the wild-type baculovirus genome is typically replaced with a recombinant gene or cDNA. These genes are commonly under the control of the polyhedrin or p10 baculovirus promoters.

The most common baculovirus used for gene expression is Autographa californica nucleopolyhedrovirus (AcNPV). AcNPV has a large (130 kb), circular, double-stranded DNA genome. The gene of interest (GOI) is cloned into a transfer vector containing a baculovirus promoter flanked by baculovirus DNA derived from a nonessential locus, such as the polyhedrin gene. The recombinant baculovirus containing the GOI is produced by homologous recombination in insect cells between the transfer vector and the genome of the parent virus (such as AcNPV).

A "translational enhancer" is a nucleotide sequence forming an element, which can promote translation and, thereby, increase protein production. Typically, a translational enhancer may be found in the 5' and 3' untranslated regions (UTRs) of mRNAs. In particular, nucleotides in the 5'-UTR immediately upstream of the initiating ATG codon of the GOI may have a profound effect on the level of translation initiation.

A virus "capsid" is commonly understood in the art as the protein shell of a virus, typically enclosing its genetic material.

A "capsid precursor protein" is a precursor of one or more structural proteins, also called capsid proteins, which takes part in the formation of a virus capsid or of a building block thereof. FMDV capsid precursor proteins typically comprise the structural protein P1. Since the protein P1 is processed by the FMDV 3C protease (3Cpro) into the mature VP0, VP3, and VP1 proteins, the P1 protein may also be referred to as polyprotein or proprotein. In the context of the present invention, the FMDV capsid precursor protein typically comprises at least P1 including the proteins VP1, VP2, VP3 and VP4. Alternatively, the FMDV capsid precursor protein may comprise one or more of the proteins VP1, VP2, VP3 and VP4. The FMDV capsid precursor protein may also comprise the protein VP0 comprising the proteins VP2 and VP4. Most preferably, the FMDV capsid precursor protein at least comprises the P1 and 2A proteins (also referred to herein as P1-2A capsid precursor).

A "virus-like particle" (VLP), which may also be referred to in the art as "empty capsid", is an entity which comprises the protein shell of a virus but lacks the RNA or DNA genome. A VLP should be antigenic and immunogenic in the same way as the wild-type virus because it retains the same structural epitopes, but it should produce no infection, due to the lack of the virus genome. An FMDV VLP is typically formed from the P1-2A capsid precursor. As described above, the 2A protease cleaves itself at its C terminus to release P1-2A from P2. Processing of the P1-2A capsid precursor is affected by the 3C protease to produce 2A and the capsid proteins VP0, VP3 and VP1. The VLP is formed by self-assembly from these capsid proteins.

VLPs may also be produced in the baculovirus expression system of the present invention using a modified 3C protease that is less toxic to the insect cells (Porta et al. (2013) J Virol Methods). Intermediate and non-toxic activity of the 3C enzyme in a P1-2A-3C expression cassette allows recombinant expression and processing of the P1-2A precursor into the structural proteins, VP0, VP1, and VP3, which assemble into VLPs. The production of VLPs may be investigated or verified using techniques known in the art such as sucrose density centrifugation or electron microscopy (Abrahams et al (1995)). Monoclonal antibodies may be used specific for conformational epitopes on the wild-type virus in order to investigate whether the structure and antigenicity of the empty capsid is retained.

The term "vaccine" as used herein refers to a preparation which, when administered to a subject, induces or stimulates a protective immune response. A vaccine can render an organism immune to a particular disease.

To "protect an animal against an infection with FMDV" means aiding in preventing, ameliorating or curing a pathogenic infection with FMDV, or aiding in preventing, ameliorating or curing a disorder arising from that infection, for example to prevent or reduce one or more clinical signs resulting from a post treatment (i.e. post vaccination) infection with FMDV.

The term "prevention" or "preventing" is intended to refer to averting, delaying, impeding or hindering the FMDV infection by a prophylactic treatment. The vaccine may, for example, prevent or reduce the likelihood of an infectious FMDV entering a cell.

Baculovirus Expression Vector

The baculovirus expression vector of the first aspect of the present invention is capable of recombinantly expressing an FMDV capsid precursor protein under control of a promoter. In particular, the baculovirus expression vector of the present invention contains an expression cassette including the initiation sequence as described herein and comprising a nucleic acid sequence encoding an FMDV capsid precursor protein, which is expressed in a host cell under control of a functional promoter.

The baculovirus expression vector of the first aspect of the present invention is capable of recombinantly expressing an FMDV capsid precursor protein under control of a promoter. The expression vector comprises the nucleic acid sequence at position −4 to −1 of 5"-AAAT-3". It has surprisingly been found in the present invention that the nucleic acid sequence 5"-AAAT-3" (also referred herein as "initiation sequence" can enhance the recombinant expression of the FMDV capsid precursor protein in a host cell.

The baculovirus expression vector of the invention may further comprise one or more restriction sites for cleavage by one or more restriction enzymes between the nucleic acid sequence at position −4 to −1 of 5'-AAAT-3' and the promoter. The one or more restriction site is not particularly limited but may be any restriction site conventionally used in the art for cloning procedures, such as a BstEII restriction site. Suitable restriction sites for cleavage by one or more restriction enzymes are well known to the skilled person and are available, for example, via the REBASE® Restriction Enzyme Database (rebase.neb.com/).

In a preferred embodiment of the invention, the nucleic acid sequence preceding the ATG start codon of an open reading frame encoding the FMDV capsid precursor protein at position −11 to −1 has the nucleic acid sequence 5"-GGTAACCAAAT-3' (SEQ ID NO. 1).

The baculovirus expression vector of the invention may further comprise one or more cis-acting elements, such as translational enhancers. The translational enhancers may be selected from one or more translational enhancers known in the art and commonly used in the field for enhancing the recombinant expression of proteins, such as FMDV capsid precursor proteins.

In a preferred embodiment, the translational enhancer comprises the translational enhancer "Syn21", which is an AT-rich synthetic sequence of 21 nucleotides (nt) made by combining the Cavener consensus sequence with elements from the *Malacosoma neustria* nucleopolyhedrovirus (MnNPV) polyhedrin gene as described in "B. D. Pfeiffer et al, PNAS (2012), Vol. 109(17), p. 6626-6631". The nucleic acid sequence of the Syn21 translational enhancer may have a nucleic acid sequence corresponding to the nucleic acid sequence 5'-AAC TTA AAA AAA AAA ATC AAA-3' (SEQ ID NO.2). In this invention, the translational enhancer Syn21 is typically located within the 5' untranslated region (UTR) of the nucleic acid sequence encoding the FMDV capsid precursor protein. In a further preferred embodiment, the nucleic acid sequence of SEQ ID NO. 2 precedes the nucleic acid sequence of SEQ ID NO. 1. Hence, the nucleic acid sequence in the baculovirus expression vector of the present invention may have the order of:

5'-SEQ ID NO.2-SEQ ID NO.1-ATG-ORF(FMDV coding region)-3'

In a further preferred embodiment, the translational enhancer comprises the "P10UTR", which is typically located within the 3' UTR of the nucleic acid sequence encoding the FMDV capsid precursor protein. The term "P10UTR" as used herein relates to the 3' UTR from the AcNPV p10 gene as described in "Y. Liu et al., Biotechnol. Lett. (2015), Vol. 37, p. 1765-1771". Preferably, the P10UTR has a nucleic acid sequence corresponding to the nucleic acid sequence of SEQ ID NO. 3.

Further preferably, the baculovirus expression vector of the invention comprises both the Syn21 and the P10UTR translational enhancers. In this preferred embodiment, the nucleic acid sequence in the baculovirus expression vector of the present invention may have the order of:

5'-SEQ ID NO.2-SEQ ID NO.1-ATG-ORF(FMDV
coding region)-SEQ ID NO.3-3'

Encompassed by the terms "Syn21" and "P10UTR" are nucleic acid sequences corresponding to those of SEQ ID NO. 2 and 3, but including conservative modifications, such as mutation and/or natural variation, of one or more nucleic acids. A modification may be a deletion or addition of one or more nucleotides or a replacement of one or more nucleotides by one or more other nucleotides. A conservative modification is typically a modification that does not substantially alter the function of the sequence as translational enhancer, i.e. the modified sequence is still capable of enhancing expression under control of the promotor of the expression cassette.

The FMDV capsid precursor protein is recombinantly expressed under the control of a suitable promoter. The promoter is not particularly limited but may be any promoter capable for the recombinant expression of the FMDV capsid precursor protein in a baculovirus expression system. Preferred promoters for use in the baculovirus expression system of the present invention are the polyhedrin (polh) promoter (described in: Ayres M. D. et al., Virology (1994), Vol. 2020, p. 586-605) and the p10 promoter (described in: Knebel D. et al., EMBO J. (1985) Vol. 4(5), 1301-1306) of AcNPV. Another preferred promoter is the promoter of the orf46 viral gene of *S. exigua* nucleopolyhedrovirus (SeNPV) (described in M. Martinez-Solis et al., PeerJ (2016), DOI 10.7717/peerj.2183).

Baculovirus expression vectors for use in baculovirus expression systems for the recombinant expression of proteins are commercially available and are extensively used in the art for the production of proteins and virus-like particles. The systems may encompass, for example, one or more transfer plasmids used to transform cells, such as *E. coli* cells or insect cells, in which the baculovirus expression vector is propagated. Commercially available baculovirus expression vectors include, but are not limited to, Top-Bac® vector (ALGENEX, Spain), pFastBac® vector (Thermo Fisher Scientific, Germany), flashBAC® vector (Oxford Expression Technologies Ltd, UK) and BestBac® vector (EXPRESSION SYSTEMS, CA).

The nucleic acid sequence encoding the FMDV capsid precursor protein is not particular limited and may be of any FMDV serotype, such as of serotypes A, O, Asia1, SAT1, SAT2, SAT3 and C. In a particularly preferred embodiment, the FMDV capsid precursor protein is from the Asia1 or SAT2 serotype.

In the baculovirus expression vector of the present invention, the capsid precursor protein typically comprises at least the capsid precursor P 1. More preferably, the capsid precursor protein comprises the capsid precursor P1 and the 2A peptide.

In a further preferred embodiment, the baculovirus expression vector of the present invention further comprises a nucleic acid sequence encoding a protease capable of cleaving an FMDV capsid precursor protein into one or more capsid proteins. The protease may be any protease capable of cleaving the FMDV capsid precursor protein as a step in the production and assembly of capsids to produce FMDV VLPs. As mentioned above, for FMDV, proteolytic processing of the precursor P1 into VP0 (VP2 plus VP4), VP3 and VP1 occurs by means of the viral 3C protease or its precursor 3CD. Hence, the protease is preferably the 3C protease of FMDV. The sequence of FMDV wild-type 3C protease from an FMDV type A strain is described in the art and is disclosed, e.g., in WO 2011/048353, which is hereby incorporated by reference in its entirety. The 3C protease may also be a functional derivative including one or more mutations, which reduce its proteolytic activity, for example a mutation at Cysteine 142.

In a further preferred embodiment, the baculovirus expression vector of the first aspect thus may be a nucleic acid sequence which further comprises a nucleic acid sequence encoding a protease. The nucleic acid sequences of the FMDV capsid precursor protein and the protease are preferably arranged in a contiguous manner. There may be a nucleic acid sequence between nucleic acid sequences encoding the FMDV capsid precursor protein and the protease. A control element, such as a control element as described in WO 2011/048353, may be present in that sequence, such that it controls expression of the protease but does not control or affect expression of the capsid precursor protein.

The capsid precursor protein may be cleavable by the protease into one or more capsid proteins to form (part of) a virus-like particle (VLP). The precursor protein may comprise all proteins necessary to form a VLP.

The capsid precursor protein may be P1, which is cleaved by the 3C protease into VP0, VP3 and VP1. Alternatively, the capsid precursor protein may be P1-2A. The 2A peptide cleaves itself at its C terminus to release P1-2A from any downstream protein sequence. Most preferably, the baculovirus expression system expresses a P1-2A-3C cassette, i.e. it simultaneously expresses the coding regions for the proteins P1, 2A and 3C. Expression of the 3C enzyme in a P1-2A-3C cassette allows expression and processing of the P1-2A precursor into the structural proteins which assemble into VLPs. The capsid precursor protein and the protease may be expressed under control of individual promotors or under control of the same promoter. For example, the capsid precursor protein may be expressed under control of a first promoter as described herein and wherein gene expression is enhanced by the initiation sequence as described herein, and the protease is expressed under control of a separate (second) promoter, which may be different from the first promoter.

Cleavage of the capsid precursor protein or VLP may be analysed using techniques known in the art. For example, extracts from baculovirus-infected host cells may be separated by gel-electrophoresis and the separated proteins transferred onto a nitrocellulose membrane for Western blotting. Western blotting with protein-specific antibodies should reveal the degree of protease-mediated cleavage. For example, for FMDV, the unprocessed capsid precursor protein (P1-2A) would appear as a band of around 81 kDa, and cleavage may produce VP3-1 (~47 kDa), VP0 (~33 kDa), VP2 (~22 kDa), VP3 (~24 kDa) and/or VP1 (~24 kDa).

Host Cell

In a second aspect, the invention provides a host cell comprising the baculovirus expression vector according to the first aspect of the invention. In a further embodiment, the host cell is capable of producing capsid precursor proteins, and preferably is capable of producing FMDV VLPs.

The host cell may, for example, be a bacterial cell, an insect cell, plant cell or a mammalian cell. Preferably, the host cell is an insect cell, such as a Sf9 cell (a clonal isolate of *Spodoptera frugiperda* Sf21 cells), or a Tni cell (ovarian cells isolated from *Trichoplusia ni*). Most preferably, the host cell is a Tni cell, or a Tni-derived cell line, such as a Tnao38 cell.

Infection of host cells, such as insect cells, can be performed by standard methods well known to the skilled person. For example, commercial suppliers of baculovirus expression systems typically provide suitable instruction manuals, which can be followed, such as the Invitrogen ° "Guide to Baculovirus Expression Vector Systems (BEVS) and Insect Cell Culture Techniques".

Method of Producing Virus-Like Particles

In a third aspect, the invention provides a method of producing FMDV capsid precursor protein. Alternatively, the invention provides a method of producing FMDV VLPs. The method according to the third aspect comprises the steps of:

(i) infecting a host cell according to the second aspect with the baculovirus expression vector according to the first aspect, and (iia) harvesting FMDV capsid precursor protein produced by the host cell, or (iib) harvesting FMDV VLPs produced by the host cell.

The method thus includes the culturing of the host cell under conditions suitable for the host cell to express the capsid precursor protein from the baculovirus expression vector in order to produce capsid precursor protein.

In case the baculovirus expression construct further expresses a protease capable of cleavage of the capsid precursor protein into one or more capsid proteins, which assemble into VLPs, as described above, FMDV VLPs may be produced by the host cell.

If the capsid precursor protein or the VLPs are released by the host cell, they may be harvested from the cell culture medium. If the capsid precursor protein or the VLPs are retained inside the host cell, they may be harvested by, for example, (i) lysis of the host cells (for example by freeze-thawing); and optionally (ii) concentration (e.g. by PEG-precipitation), and/or (iii) purification.

Vaccines and Production Thereof

The present invention further relates to the production of FMDV VLPs, which are used in the production of a vaccine.

The present invention thus also provides a method for the production of a vaccine, which comprises the step of producing FMDV VLPs by a method according to the third aspect and incorporating the FMDV VLPs in a vaccine, such as by the addition of a pharmaceutically acceptable carrier.

Pharmaceutically acceptable carriers are well-known in the art. Merely as an example; such a carrier can be as simple as sterile water or a buffer solution such as PBS. The vaccine may comprise a single carrier or a combination of two or more carriers. The vaccine may also comprise one or more pharmaceutically acceptable diluents, adjuvants and/or excipients. The vaccine may also comprise, or be capable of expressing, another active agent, for example one which may stimulate early protection prior to the vaccinating entity-induced adaptive immune response. The agent may be an antiviral agent, such as type I interferon. Alternatively, or in addition, the agent may be granulocyte-macrophage colony-stimulating factor (GM-CSF).

The vaccine may be used therapeutically, to treat an existing FMDV infection (especially in herds or regions where the virus is endemic), but preferably is used prophylactically, to block or reduce the likelihood of FMDV infection and/or prevent or reduce the likelihood of spreading the disease.

Many commercially available FMD vaccines are multivalent to provide protection against the different FMD serotypes. By the same token, the vaccine of the present invention may comprise a plurality of vaccinating entities, each directed at a different serotype and/or different subtypes within a given serotype.

Treatment

The present invention also provides a method of protecting a subject against an infection with FMDV by administration of an effective amount of a vaccine of the present invention.

For FMD the subject may be a cloven-hoofed animal. FMD susceptible animals include cattle, sheep, pigs, and goats among farm stock, as well as camelids (camels, llamas, alpacas, guanaco and vicuna). Some wild animals such as hedgehogs, coypu, and any wild cloven-footed animals such as deer and zoo animals including elephants are also susceptible to FMD.

Administration

The present invention contemplates at least one administration to an animal of an efficient amount of the vaccine according to the invention. A vaccine can be administered in any art-known method, including any local or systemic method of administration. Administration can be performed e.g. by administering the antigens into muscle tissue (intramuscular, IM), into the dermis (intradermal, ID), underneath the skin (subcutaneous, SC), underneath the mucosa (submucosal, SM), in the veins (intravenous, IV), into the body cavity (intraperitoneal, IP), orally, anally etc. For the current vaccine IM, ID and SC administration are preferred.

EXAMPLES

The invention will be further described by way of the following non-limiting examples, which are meant to serve to assist one of ordinary skill in the art in carrying out the invention.

The standard baculovirus expression vector as described by Porta et al (2013; J Virol Methods) contains the BstEII restriction enzyme site upstream of the ATG start codon of the P1-2A-3C expression cassette. It was evaluated if the 5'-AAAT-3' sequence that precedes the highly expressed polyhedrin gene of AcNPV can improve translation of the P1-2A-3C expression cassette.

Two versions of the initiation sequence upstream of the ATG start codon were compared. The version used as the comparative Example does not contain a special sequence upstream of the ATG start codon, just the BstEII restriction enzyme site (GGTTACCATGGG; designated in the following as "Standard", SEQ ID NO. 4). The version according to the invention has the 5'-AAAT-3' sequence between the BstEII site and the ATG codon and contains a single nucleotide change in the BstEII site (GGTAACCAAATATGGG; designated in the following as "AAAT", SEQ ID NO. 5).

Baculovirus expression plasmids used in Examples 1-4 were based on the standard baculovirus transfer vector pFastBac® (Thermo Fisher Scientific, Germany), in which expression is driven by the polyhedrin (polh) promoter. The expression plasmids comprising a nucleic acid sequence encoding a P1-2A-3C capsid precursor protein were obtained by using standard cloning procedures well known in the art. The nucleic acid sequences of the expression plasmids are according to SEQ ID NO. 6-9.

Example 1—Expression of P1-2A-3C Expression Cassette Based on FMDV Asia1 Serotype In this Example, the expression level of an FMDV capsid precursor protein of an Asia1 serotype from the "AAAT"

expression cassette is compared to the expression from the "standard" expression cassette without the AAAT sequence.

Erlenmeyer flasks with 100 ml containing $3.2 \times 10^5$ cells/ml of Tni cells were infected at MOI=1 with recombinant baculoviruses containing the P1-2A-3C expression cassette based on Asia1/Irn/49/11 VP2-S93Y of FMDV Asia1 serotype. The culture was harvested at 4 dpi and the cells were collected by centrifugation and subsequently sonicated in Tris-KCl pH8.0 buffer at one-tenth of the original 35 culture volume.

Samples were analyzed by Western blotting using the anti-VP0 monoclonal antibody as described by: Loureiro S. et al., Wellcome Open Res 2018, 3:88.

Visual inspection of the Western blot shows that the standard baculovirus vector performs less than the AAAT-containing vector in terms of yield of FMDV-related proteins, and the difference is estimated at 2-fold (FIG. 1).

Example 2—Expression of P1-2A-3C Expression Cassette Based on FMDV SAT2 Serotype In this Example, the expression level of an FMDV capsid precursor protein of a SAT2 serotype from the "AAAT" expression cassette is compared to the expression from the "standard" expression cassette without the AAAT sequence.

Tni cells infected with recombinant baculoviruses containing the P1-2A-3C expression cassette based on SAT2/Egy/2/12 VP2-K93Y of FMDV SAT2 serotype were cultivated and the culture was harvested as described in Example 1.

Samples were analyzed by Western blotting using a cocktail of 5 SAT2-specific monoclonal antibodies: 1D5, DA10, GE11, GD12, and GG1 as described by: Opperman et al., 2014, J Virol. Visual inspection of the Western blot shows that the standard baculovirus vector performs less than the AAAT-containing vector in terms of yield of FMDV-related proteins, and the difference is estimated at 2-fold (FIG. 2; note that the 2 proteins on the blot, VP1 and VP1+VP3 are indicated based on size and reaction pattern, but that it has not been validated which FMDV proteins are detected by the cocktail of 5 monoclonal antibodies).

Example 3—Expression of P1-2A-3C Expression Cassette Based on FMDV 0 Serotype In this Example, the expression level of an FMDV capsid precursor protein of an O serotype from the "AAAT" expression cassette is compared to the expression from the "standard" expression cassette without the AAAT sequence.

Tni cells infected with recombinant baculoviruses containing the P1-2A-3C expression cassette based on O/Tur/5/09 VP2-S93F of FMDV O serotype were cultivated and the culture was harvested as described in Example 1. In addition to the cells, supernatant samples were collected after the centrifugation step described in Example 1. Supernatant samples represent the cell culture fluid without the cells.

Cell and supernatant samples were analyzed by Western blotting using the anti-VP0 monoclonal antibody as described by: Loureiro S. et al., Wellcome Open Res 2018, 3:88. Visual inspection of the Western blot shows that the standard baculovirus vector performs better than the AAAT-containing one in terms of yield of FMDV-related proteins (FIG. 3).

Example 4—Expression of P1-2A-3C Expression Cassette Based on FMDV a Serotype In this Example, the expression level of an FMDV capsid precursor protein of an A serotype from the "AAAT" expression cassette is compared to the expression from the "standard" expression cassette without the AAAT sequence.

Tni cells infected with recombinant baculoviruses containing the P1-2A-3C expression cassette based on A/Irn/7/13 VP2-H93F of FMDV A serotype were cultivated and the culture was harvested as described in Example 3.

Cell and supernatant samples were analyzed by Western blotting using polyclonal cattle serum (MSD Animal Health, NL). Visual inspection of the Western blot suggests that the standard baculovirus vector performs equally well as or maybe slightly better than the AAAT-containing one in terms of yield of FMDV-related proteins (FIG. 4).

Summary of Results:

TABLE 1

Results of recombinant expression of capsid precursor protein

| Example | Capsid precursor protein | Relative expression Approx. fold (AAAT/standard) |
|---|---|---|
| 1 | Asia1/Irn/49/2011 VP2-S93Y | 2.0× |
| 2 | SAT2/Egy/02/2012 VP2-K93Y | 2.0× |
| 3 | O/Tur/05/2009 VP2-S93F | 0.4× |
| 4 | A/Irn/07/2013 VP2-H93F | 1.0× |

Examples 1-4 show that recombinant expression of capsid precursor proteins originating from Asia1 and SAT2 serotypes was surprisingly higher for expression constructs with the AAAT sequence included compared to expression constructs including the standard ATG initiation sequence (see Table 1 for a summary).

---

The invention claimed is:

1. A baculovirus expression vector for recombinantly expressing a Foot and mouth disease virus (FMDV) capsid precursor protein, the expression vector comprising a nucleic acid sequence encoding the FMDV capsid precursor protein under the control of a promoter, wherein the ATG start codon of an open reading frame encoding the FMDV capsid precursor protein is preceded at position −4 to −1 by the nucleic acid sequence 5'-AAAT-3' and wherein the FMDV is of the Asia1 or SAT2 serotype.

2. The baculovirus expression vector according to claim 1, the vector further comprising one or more restriction sites for cleavage by one or more restriction enzymes between the nucleic acid sequence at position −4 to −1 of 5'-AAAT-3' and the promoter.

3. The baculovirus expression vector according to claim 1, having the nucleic acid sequence 5'-GGTAACCAAAT-3' (SEQ ID NO. 1) at position −11 to −1.

4. The baculovirus expression vector according to claim 1, wherein expression of the FMDV capsid precursor protein is achieved under the control of the baculovirus polyhedrin promoter (polh) or p10 promoter.

5. The baculovirus expression vector according to claim 1, wherein the capsid precursor protein comprises the capsid precursor P1.

6. The baculovirus expression vector according to claim 1, the vector further comprising a nucleic acid sequence encoding a protease capable of cleaving the capsid precursor protein into one or more capsid proteins.

7. The baculovirus expression vector according to claim 6, wherein the capsid precursor protein comprises the capsid precursor P1 and the peptide 2A and the protease is 3C.

8. A host cell comprising the baculovirus expression vector according to claim 1.

9. The host cell according to claim 8, which is an insect cell.

10. A method of producing FMDV capsid precursor protein, the method comprising the steps of:
   (i) infecting a host cell with the baculovirus expression vector according to claim 1, and
   (ii) harvesting FMDV capsid precursor protein produced by the host cell.

11. A method of producing FMDV virus-like particles (VLPs), the method comprising the steps of:
   (i) infecting a host cell with the baculovirus expression vector according to claim 6, and
   (ii) harvesting FMDV VLPs produced by the host cell.

12. A method of producing a vaccine, which comprises the steps of:

(i) producing FMDV virus-like particles (VLPs) by the method according to claim 11 and (ii) incorporating the FMDV VLPs into a vaccine by addition of a pharmaceutically acceptable carrier.

13. A method of protecting a subject against an infection with FMDV, which comprises the step of expressing an FMDV capsid precursor protein from the baculovirus expression vector according to claim 1 in a host cell to produce a VLPs, incorporating the VLPs into a vaccine by addition of a pharmaceutically acceptable carrier and administering the vaccine to the subject.

\* \* \* \* \*

SEQUENCE LISTING

<160> NUMBER OF SEQ ID NOS: 9

<210> SEQ ID NO 1
<211> LENGTH: 11
<212> TYPE: DNA
<213> ORGANISM: Artificial Sequence
<220> FEATURE:
<223> OTHER INFORMATION: Initiation Sequence -1 to -11

<400> SEQUENCE: 1
ggtaaccaaa t                                                          11

<210> SEQ ID NO 2
<211> LENGTH: 21
<212> TYPE: DNA
<213> ORGANISM: Artificial Sequence
<220> FEATURE:
<223> OTHER INFORMATION: Syn21 translational enhancer

<400> SEQUENCE: 2
aacttaaaaa aaaaaatcaa a                                                          21

<210> SEQ ID NO 3
<211> LENGTH: 666
<212> TYPE: DNA
<213> ORGANISM: Artificial Sequence
<220> FEATURE:
<223> OTHER INFORMATION: P10UTR translational enhancer

<400> SEQUENCE: 3
atgaatcgtt tttaaaataa caaatcaatt gttttataat attcgtacga ttctttgatt       60
atgtaataaa atgtgatcat taggaagatt acgaaaaata taaaaaatat gagttctgtg      120
tgtataacaa atgctgtaaa cgccacaatt gtgtttgttg caaataaacc cagtattatt      180
tgattaaaat tgttgttttc tttgttcata dacaatagtg tgttttgcct aaacgtgtac      240
tgcataaact ccatgcgagt gtatagcgag ctagtggcta acgcttgccc caccaaagta      300
gattcgtcaa aatcctcaat ttcatcaccc tcctccaagt ttaacatttg gccgtcggaa      360
ttaacttcta aagatgccac ataatctaat aaatgaaata gagattcaaa cgtggcgtca      420
tcgtccgttt cgaccatttc cgaaaagaac tcgggcataa actctatgat ttctctggac      480
gtggtgttgt cgaaactctc aaagtacgca gtcaggaacg tgcgcgacat gtcgtcggga      540
aactcgcgcg gaaacatgtt gttgtaaccg aacgggtccc atagcgccaa aaccaaatct      600
gccagcgtca atagaatgag cacgatgccg acaatggagc tggcttggat agcgattcga      660
gttaac                                                                          666

<210> SEQ ID NO 4
<211> LENGTH: 12
<212> TYPE: DNA
<213> ORGANISM: Artificial Sequence
<220> FEATURE:
<223> OTHER INFORMATION: Standard" Initiation Sequence

<400> SEQUENCE: 4
ggttaccatg gg                                                                   12

<210> SEQ ID NO 5
<211> LENGTH: 16
<212> TYPE: DNA
<213> ORGANISM: Artificial Sequence
<220> FEATURE:
<223> OTHER INFORMATION: BstEII-AAAT-Initiation Sequence -11 to +5

<400> SEQUENCE: 5
ggtaaccaaa tatggg                                                               16

<210> SEQ ID NO 6
<211> LENGTH: 7737
<212> TYPE: DNA
<213> ORGANISM: Artificial Sequence
<220> FEATURE:
<223> OTHER INFORMATION: pFastBac Asia1_IRN_49_11 VP2-S93Y -continued

<400> SEQUENCE: 6

```
ggatccggta accaaatatg ggtgctggac aatcatctcc cgctactggc tctcaaaacc      60
aatcaggcaa cactggatct atcatcaaca actactacat gcaacaatac caaaacagca     120
tggacaccca actgggagac aacgctatct caggcggtag caacgagggc agcaccgaca     180
ccacttctac tcacaccact aacacccaaa acaacgactg gttctctaag ctcgcaagct     240
ctgccttctc aggtctgttc ggagctcttc ttgccgacaa gaaaaccgag gaaaccactc     300
tcctggagga ccgtatcctg accactcgta acggccacac cactagcacc actcaatcaa     360
gcgttggagt gacttacggc tacgctaccg ccgaagacgc tgtgtcaggc cccaacacta     420
gcggtctgga gacccgtgtt caacaagctg aacgtttctt caagaaacat ctgttcgact     480
ggacccccaa ccttgctttc ggctactgcc actacctgga gctgcccacc gaccataagg     540
gcgtttacgg gtacctgatg gactcatacg cttacatgcg taacggatgg gacatcgaag     600
ttaccgccgt gggcaaccaa ttcaacggag gctgtcttct cgttgctctt gtgcccgaac     660
ttaagtcact cgacactcgt caaaaatacc aacttaccct cttcccccac caattcatca     720 accccccgtac caacatgact gctcatatca gcgttccctt cgttggcgtg aaccgttacg     780
accaataccg tatgcacaag ccctggacac tagttgtgat ggttgtggct cccctcaccg     840
tgaagactgg tggaagcgaa caaatcaaag tttacatgaa cgctgccccc acctacgttc     900
atgtggctgg cgagctgccc tctaaggaag gaatcgttcc cgtggcttgc gccgacggat     960
acggcaacat ggttactact gaccccaaga ccgctgaccc cgtgtacggc aaagttttca    1020
accctccccg tactaacctg cccggtcgtt tcaccaactt ccttgacgtt gctgaggcgt    1080
gtcccacctt cctccgtttc ggtgaagttc ccttcgtgaa gaccgttaac tctggagacc    1140
gtctgcttgc taaattcgac gttagcctgg ctgccggtca catgtctaac acctacctgg    1200
ctggacttgc ccaatactac actcaataca gcggcaccat gaacatccat ttcatgttca    1260
ccggtcccac tgacgctaag gcccgttaca tggtggctta cgttcctccc ggaatgaccc    1320
ctcccactga gcccgaacgt gctgctcact gcatccatag cgagtgggac actggcctca    1380
actctaagtt caccttctca atcccctacc tgagcgctgc agactacgct tacaccgcct    1440
cagacgttgc tgaaaccact agcgtgcaag ctgggtttg tatctaccaa atcacccacg    1500
gcaaggctga gggagacgcc ctggttgtgt ctgtgtcagc tggaaaagac ttcgaatttc    1560
gtcttcccgt tgacgctcgt cgtcaaacca ccaccgctgg agagagcgct gaccccgtga    1620 ctaccactg tgagaactac ggcggtgaaa ctcaagctgc tcgtcgtctg cacaccgacg    1680
tgggattcgt tcttgaccgt ttcgtgaagc tcaccaaccc caaagctacc caaactctgg    1740
accttatgca aatccctccc tacactctgg ttggcgctct cctgcgttct gccacctact    1800
acttctcaga cctcgaagtg gctctggttc acaccggccc cgtgacttgg gttcccaacg    1860
gtgctcccaa gaccgcccct tgactgccaaa ccaaccccac tgcttaccaa aaacaaccca    1920
tcactcgtct cgctctgccc tacaccgctc cccaccgtgt gctagctact gtttacaacg    1980
gaaagaccgc ttacggaccc gaggctcccc gtcgtggcga cctggctgcc atcgctcaac    2040
gtgtgagcac ctctctcccc actagcttca actacgcgc tgttaaggcc gagaacatca    2100
ctgaacttct catccgtatg aaacgtgctg aaacctactg ccccgtccc ctgcttgctc    2160 tggacaccac tcaagaccgt cgtaagcaag agatcatcgc tcccgaaaaa caagtgctga    2220
acttcgacct gctcaaactc gctggtgacg tggaatctaa ccccgaccc agcggccgcg    2280 gaccttttt agggaagatc tggccttcct acaagggaag gccagggaat tttcttacga    2340
```

-continued

```
gggacctgtg aagaagcctg tcgctttgaa agtgaaagct aagaacttga ttgtcactga    2400
gagtggagcc ccaccgaccg acttgcaaaa gatggtcatg ggcaacacca agcctgttga    2460
gcttatcctc gacgggaaga cggtggccat ttgttgtgct accggagtgt ttggcactgc    2520
gtacctcgtg cctcgtcatc tttttgcaga aaaatatgac aagatcatgc tggacggcag    2580
agccatgaca gacagtgact acagagtgtt tgaattcgag attaaagtaa aaggacagga    2640
catgctctca gacgctgcgc tcatggtact ccaccgtggg aatcgcgtga gagacatcac    2700
gaaacacttt cgtgacacag caagaatgaa gaaaggcacc cctgttgtcg gagtgatcaa    2760
caatgccgac gttgggagac tgatcttctc tggtgaggcc ttaacctaca aggacattgt    2820
agtgactatg gatggagaca ccatgcctgg cctgtttgcc tacaaagccg ccaccaaggc    2880
tggctactgt gggggagccg ttcttgctaa ggacggagct gacacattca tcgttggtac    2940
ccactccgca ggcggcaatg gagttggata ctgctcatgc gtctcgaggt ccatgttgct    3000
gaaaatgaag gcgcacatcg accccgaacc acaccacgag taatctagag gatcccctca    3060
ggaagcttag cttgtcgaga agtactagag gatcataatc agccatacca catttgtaga    3120
ggttttactt gctttaaaaa acctcccaca cctccccctg aacctgaaac ataaaatgaa    3180
tgcaattgtt gttgttaact gtttattgc agcttataat ggttacaaat aaagcaatag    3240
catcacaaat ttcacaaata aagcattttt ttcactgcat tctagttgtg gtttgtccaa    3300
actcatcaat gtatcttatc atgtctggat ctgatcactg cttgagccta ggagatccga    3360
accagataag tgaaatctag ttccaaacta ttttgtcatt tttaatttc gtattagctt    3420 acgacgctac acccagttcc catctatttt gtcactcttc cctaaataat ccttaaaaac    3480
tccatttcca cccctcccag ttcccaacta ttttgtccgc ccacagcggg gcatttttct    3540
tcctgttatg ttttaatca aacatcctgc caactccatg tgacaaaccg tcatcttcgg    3600
ctactttttc tctgtcacag aatgaaaatt tttctgtcat ctcttcgtta ttaatgtttg    3660
taattgactg aatatcaacg cttatttgca gcctgaatgg cgaatggacg cgccctgtag    3720
cggcgcatta agcgcggcgg gtgtggtggt tacgcgcagc gtgaccgcta cacttgccag    3780
cgccctagcg cccgctcctt tcgctttctt cccttccttt ctcgccacgt tcgccggctt    3840
tccccgtcaa gctctaaatc gggggctccc tttagggttc cgatttagtg ctttacggca    3900
cctcgacccc aaaaaacttg attagggtga tggttcacgt agtgggccat cgccctgata    3960
gacggttttt cgccctttga cgttggagtc cacgttcttt aatagtggac tcttgttcca    4020
aactggaaca cactcaacc ctatctcggt ctattctttt gatttataag ggattttgcc    4080
gatttcggcc tattggttaa aaaatgagct gatttaacaa aaatttaacg cgaattttaa    4140
caaaatatta cgtttacaa tttcaggtgg cacttttcgg ggaaatgtgc gcggaacccc    4200 tatttgtttta tttttctaaa tacattcaaa tatgtatccg ctcatgagac aataaccctg    4260
ataaatgctt caataatatt gaaaaaggaa gagtatgagt attcaacatt ccgtgtcgc    4320 ccttattccc ttttttgcgg cattttgcct tcctgttttt gctcacccag aaacgctggt    4380
gaaagtaaaa gatgctgaag atcagttggg tgcacgagtg ggttacatcg aactggatct    4440
caacagcggt aagatccttg agagttttcg ccccgaagaa cgttttccaa tgatgagcac    4500
ttttaaagtt ctgctatgtg gcgcggtatt atcccgtatt gacgccgggc aagagcaact    4560
cggtcgccgc atacactatt ctcagaatga cttggttgag tactcaccag tcacagaaaa    4620
gcatcttacg gatggcatga cagtaagaga attatgcagt gctgccataa ccatgagtga    4680
```

```
taacactgcg gccaacttac ttctgacaac gatcggagga ccgaaggagc taaccgcttt    4740
tttgcacaac atgggggatc atgtaactcg ccttgatcgt tgggaaccgg agctgaatga    4800
agccatacca aacgacgagc gtgacaccac gatgcctgta gcaatggcaa caacgttgcg    4860
caaactatta actggcgaac tacttactct agcttcccgg caacaattaa tagactggat    4920
ggaggcggat aaagttgcag gaccacttct gcgctcggcc cttccggctg gctggtttat    4980
tgctgataaa tctggagccg gtgagcgtgg gtctcgcggt atcattgcag cactggggcc    5040
agatggtaag ccctcccgta tcgtagttat ctacacgacg gggagtcagg caactatgga    5100
tgaacgaaat agacagatcg ctgagatagg tgcctcactg attaagcatt ggtaactgtc    5160
agaccaagtt tactcatata tactttagat tgatttaaaa cttcattttt aatttaaaag    5220
gatctaggtg aagatccttt ttgataatct catgaccaaa atcccttaac gtgagttttc    5280
gttccactga gcgtcagacc ccgtagaaaa gatcaaagga tcttcttgag atcctttttt    5340
tctgcgcgta atctgctgct tgcaaacaaa aaaaccaccg ctaccagcgg tggtttgttt    5400
gccggatcaa gagctaccaa ctctttttcc gaaggtaact ggcttcagca gagcgcagat    5460
accaaatact gtccttctag tgtagccgta gttaggccac cacttcaaga actctgtagc    5520
accgcctaca tacctcgctc tgctaatcct gttaccagtg gctgctgcca gtggcgataa    5580
gtcgtgtctt accgggttgg actcaagacg atagttaccg gataaggcgc agcggtcggg    5640
ctgaacgggg ggttcgtgca cacagcccag cttggagcga cgacctaca ccgaactgag    5700 atacctacag cgtgagcatt gagaaagcgc cacgcttccc gaagggagaa aggcggacag    5760
gtatccggta agcggcaggg tcggaacagg agagcgcacg agggagcttc caggggggaaa    5820 cgcctggtat ctttatagtc ctgtcgggtt cgccacctc tgacttgagc gtcgattttt    5880
gtgatgctcg tcagggggc ggagcctatg gaaaaacgcc agcaacgcgg cctttttacg    5940
gttcctggcc ttttgctggc cttttgctca catgttcttt cctgcgttat cccctgattc    6000
tgtggataac cgtattaccg cctttgagtg agctgatacc gctcgccgca gccgaacgac    6060
cgagcgcagc gagtcagtga gcgaggaagc ggaagagcgc ctgatgcggt attttctcct    6120
tacgcatctg tgcggtattt cacaccgcag accagccgcg taacctggca aaatcggtta    6180
cggttgagta ataaatggat gccctgcgta agcgggtgtg gcggacaat aaagtcttaa    6240 actgaacaaa atagatctaa actatgacaa taaagtctta aactagacag aatagttgta    6300
aactgaaatc agtccagtta tgctgtgaaa aagcatactg gactttttgtt atggctaaag    6360 caaactcttc attttctgaa gtgcaaattg cccgtcgtat taaagagggg cgtgccaag    6420 ggcatggtaa agactatatt cgcggcgttg tgacaattta ccgaacaact ccgcggccgg    6480
gaagccgatc tcggcttgaa cgaattgtta ggtggcggta cttgggtcga tatcaaagtg    6540
catcacttct tcccgtatgc ccaactttgt atagagagcc actgcgggat cgtcaccgta    6600
atctgcttgc acgtagatca cataagcacc aagcgcgttg gcctcatgct tgaggagatt    6660
gatgagcgcg gtggcaatgc cctgcctccg gtgctcgccg gagactgcga gatcatagat    6720
atagatctca ctacgcggct gctcaaacct gggcagaacg taagccgcga gagcgccaac    6780
aaccgcttct tggtcgaagg cagcaagcgc gatgaatgtc ttactacgga gcaagttccc    6840
gaggtaatcg gagtccggct gatgttggga gtaggtggct acgtctccga actcacgacc    6900
gaaaagatca agagcagccc gcatggattt gacttggtca gggccgagcc tacatgtgcg    6960
aatgatgccc atacttgagc cacctaactt tgttttaggg cgactgccct gctgcgtaac    7020
atcgttgctg ctgcgtaaca tcgttgctgc tccataacat caaacatcga cccacggcgt    7080
```

-continued

```
aacgcgcttg ctgcttggat gcccgaggca tagactgtac aaaaaaacag tcataacaag    7140
ccatgaaaac cgccactgcg ccgttaccac cgctgcgttc ggtcaaggtt ctggaccagt    7200
tgcgtgagcg catacgctac ttgcattaca gtttacgaac cgaacaggct tatgtcaact    7260
gggttcgtgc cttcatccgt ttccacggtg tgcgtcaccc ggcaaccttg ggcagcagcg    7320
aagtcgaggc atttctgtcc tggctggcga acgagcgcaa ggtttcggtc tccacgcatc    7380
gtcaggcatt ggcggccttg ctgttcttct acggcaaggt gctgtgcacg gatctgccct    7440
ggcttcagga gatcggaaga cctcggccgt cgcggcgctt gccggtggtg ctgaccccgg    7500
atgaagtggt tcgcatcctc ggttttctgg aaggcgagca tcgtttgttc gcccaggact    7560
ctagctatag ttctagtggt tggctacgta tactccggaa tattaataga tcatggagat    7620
aattaaaatg ataaccatct cgcaaataaa taagtatttt actgttttcg taacagtttt    7680
gtaataaaaa aacctataaa tattccggat tattcatacc gtcccaccat cgggcgc       7737
```

<210> SEQ ID NO 7
<211> LENGTH: 7759
<212> TYPE: DNA
<213> ORGANISM: Artificial Sequence
<220> FEATURE:
<223> OTHER INFORMATION: pFastBac SAT2_EGY_2_12 VP2-K93Y

<400> SEQUENCE: 7

```
ggatccggta accaaatatg ggggcagggc aatcgtctcc ggctactggc tcgcagaacc      60
aatcgggaaa cactggctct atcatcaaca actactacat gcaacaatac caaaacagca     120
tggacaccca actgggcgac aacgctatct cgggcggcag caacgaaggc agcaccgaca     180 ccaccgcac tcacaccaac aatactcaaa actctgactg gttctcaaag ctggctcaga     240
gcgcaatctc tgggctcttc ggtgcgctgc ttgctgacaa gaaaaccgag gaaacgaccc     300
tcctggagga ccgtatcctg actacacgtc atggcaccac taccagcacc actcaaaagct    360 ctgttggagt gaccttcggg tacgcggacg ctgatagctt ccgtcccgga ccaaacacct    420
ctggccttga aacgcgtgtt caacaggctg agcgtttctt caaagaaaag ctgttcgact    480
ggaccagcga taaaccttc ggcactctgt acgtgctgga gcttcccaaa gaccacaagg     540
gaatctacgg ctacctgacc gacagctaca cttatatgcg taacggctgg gatgtccaag     600
ttagcgctac cagcacccag ttcaacggag gcagcctact agttgccatg gttcccgagc     660
tgtgctccct tgaaagccgt gaggagttcc aactcaccct atacccccac cagttcatca     720
accctcgtac taatacgacc gctcatattc aagttcccta ccttggtgtg aaccgtcacg     780
accaaggaaa gcgccatcaa gcctggtcac tcgttgtgat ggttctcacc cctctaacta     840
cggaggctca aatgaacagc ggcaccgttg aagtgtacgc caacatcgca cccactaatg     900
tcgtagttgc tggcgaactg ccgggcaaac aaggtattgt tcccgttgct gctgctgacg     960
gttacggcgg tttccaaaac accgacccca agaccgctga ccccatctac ggatatgttt    1020
acaacccctc gcgaaatgac tgccacggcc gtttcagcaa ccttctcgac gttgccgagg    1080
cttgccccac cctattagac ttcgatggta aaccctacat cgtgactaaa aacaatggaa    1140
acaaggttat ggcatcttc gacgttgcct tcacccacaa ggtgcatcgt aacactttcc     1200
tggctggcct tgccgactac tatacccaat actccggtag cctgaactat cacttcatgt    1260
acaccggacc cactcaccat aaaagcaaagt tcatggtggc ctacgtcccc cctggtgttg    1320
aggctaccca actgccgacc actccagaag acgcggctca ctgctaccat gctgagtggg    1380
```

-continued

```
acaccggcct gaacagcagc ttcagcttcg ctgtgcccta catcagcgct gctgacttct      1440
cttacactca caccgatact cccgcgatgg ctacgaccaa cggttgggtt atcgtgctgc      1500
aggttacgga cactcattct gctgaagctg ctgttgttgt tagcgttagc gctggccccg      1560
acctggagtt caggttcccc atcgaccccg ttcgtcaaac taccagcgct ggcgaagggg      1620
cagacgttgt gaccaccgac ccctctaccc acggagggaa cgttcaagag ggccgtcgca      1680
aacatactga agtggctttc ctgcttgacc gttcaaccca cgtccatact aacaagacga      1740
ccttcgtcgt tgacctgatg gataccaaga aaaaggctct cgttggagcc atcctgcgtg      1800
catctaccta ctatttctgc gacctcgaaa ttgcttgtgt gggcgaccac acccgtgctt      1860
tctggcaacc aaacggagca ccaaggacta cccaactggg tgacaacccc atggtcttcg      1920
ctaagggcgg tgttacccgt ttcgctatcc ccttcactgc ccctcaccgt ctgctatcta      1980
ccgtgtataa cggcgagtgc gtctacaaaa aggcaccaac cgctatcagg ggagacaggg      2040
cagctctggc tgctaagtac gctgacacta cccataccct tccctcaact ttcaacttcg      2100
gcagcgtcac cgtagaccgt cccgttgatg tgtactatcg tatgaagcgc gctgaactgt      2160
actgtccccg tcccctgcta gctgcatacg agcacgctgg aagggaccgt ttcgatgccc      2220
ccatcggcgt tgagcgtcag accctaaatt tcgacctatt aaaacaagct ggggacgttg      2280
aatcgaaccc cggacccagc ggccgcggac cttttttagg gaagatctgg ccttcctaca      2340
agggaaggcc agggaatttt cttatgaggg gccagtgaaa aagcctgtcg ccttgaaagt      2400
gaaagcaaag aacatgatca tcacggagag tggtgcaccg cccaccgact tgcaaaagat      2460
ggtgatggct aacaccaagc cggtcgagct catactcgac gggaagacag tggcaatctg      2520
ctgtgctact ggagtgtttg gaactgccta tctcgtgcct cgtcaccttt tcgctgaaaa      2580
gtacgacaag atcatgattg acggtagagc catgacagac cgtgatttca gagtgtttga      2640
attcgagatc aaagtaaagg gacaggacat gctctcagac gccgcactca tggttctgca      2700
ccgcgggaac cgcgtgagag acatcacgaa acacttcgt gatcaagcaa gaatgaggaa      2760
aggtaccccc gttgttggcg tgatcaacaa tgctgacgtc gggagactca tcttctctgg      2820
agaggcgctc acctacaaag acattgtagt gactatggat ggtgatacca tgccaggcct      2880
ctttgcctac aaggccgcca ccaaggctgg ctactgtgga ggagccgttc ttgcaaaaga      2940
cggagccgag actttcatcg tcggcactca ctccgcagga gggaacggag ttggttactg      3000
ctcctgcgtt tccaagtcca tgctcctaca aatgaaggca cacgtcgacc ccgaaccaca      3060
ccacgaataa tctagaggat cccctcagga agcttgtcga gaagtactag aggatcataa      3120
tcagccatac cacatttgta gaggttttac ttgctttaaa aaacctccca cacctccccc      3180
tgaacctgaa acataaaatg aatgcaattg ttgttgttaa cttgtttatt gcagcttata      3240
atggttacaa ataaagcaat agcatcacaa atttcacaaa taaagcattt ttttcactgc      3300
attctagttg tggtttgtcc aaactcatca atgtatctta tcatgtctgg atctgatcac      3360
tgcttgagcc taggagatcc gaaccagata agtgaaatct agttccaaac tattttgtca      3420
tttttaattt tcgtattagc ttacgacgct acacccagtt cccatctatt ttgtcactct      3480
tccctaaata atccttaaaa actccatttc caccctccc agttcccaac tattttgtcc      3540
gcccacagcg gggcattttt cttcctgtta tgttttaat caaacatcct gccaactcca      3600
tgtgacaaac cgtcatcttc ggctactttt tctctgtcac agaatgaaaa tttttctgtc      3660
atctcttcgt tattaatgtt tgtaattgac tgaatatcaa cgcttatttg cagcctgaat      3720
ggcgaatgga cgcgccctgt agcggcgcat taagcgcggc gggtgtggtg gttacgcgca      3780
```

-continued

```
gcgtgaccgc tacacttgcc agcgccctag cgcccgctcc tttcgctttc ttcccttcct    3840
ttctcgccac gttcgccggc tttccccgtc aagctctaaa tcgggggctc cctttagggt    3900
tccgatttag tgctttacgg cacctcgacc ccaaaaaact tgattagggt gatggttcac    3960
gtagtgggcc atcgccctga tagacggttt ttcgcccttt gacgttggag tccacgttct    4020
ttaatagtgg actcttgttc caaactggaa caacactcaa ccctatctcg gtctattctt    4080
ttgatttata agggattttg ccgatttcgg cctattggtt aaaaaatgag ctgatttaac    4140
aaaaatttaa cgcgaatttt aacaaaatat taacgtttac aatttcaggt ggcacttttc    4200
ggggaaatgt gcgcggaacc cctatttgtt tatttttcta aatacattca aatatgtatc    4260
cgctcatgag acaataaccc tgataaatgc ttcaataata ttgaaaaagg aagagtatga    4320
gtattcaaca tttccgtgtc gcccttattc ccttttttgc ggcattttgc cttcctgttt    4380
ttgctcaccc agaaacgctg gtgaaagtaa aagatgctga agatcagttg ggtgcacgag    4440
tgggttacat cgaactggat ctcaacagcg gtaagatcct tgagagtttt cgccccgaag    4500
aacgttttcc aatgatgagc acttttaaag ttctgctatg tggcgcggta ttatcccgta    4560
ttgacgccgg gcaagagcaa ctcggtcgcc gcatacacta ttctcagaat gacttggttg    4620
agtactcacc agtcacagaa aagcatctta cggatggcat gacagtaaga gaattatgca    4680
gtgctgccat aaccatgagt gataacactg cggccaactt acttctgaca acgatcggag    4740
gaccgaagga gctaaccgct tttttgcaca acatggggga tcatgtaact cgccttgatc    4800
gttgggaacc ggagctgaat gaagccatac caaacgacga gcgtgacacc acgatgcctg    4860
tagcaatggc aacaacgttg cgcaaactat taactggcga actacttact ctagcttccc    4920
ggcaacaatt aatagactgg atggaggcgg ataaagttgc aggaccactt ctgcgctcgg    4980
cccttccggc tggctggttt attgctgata atctggagc cggtgagcgt gggtctcgcg    5040
gtatcattgc agcactgggg ccagatggta agccctcccg tatcgtagtt atctacacga    5100
cggggagtca ggcaactatg gatgaacgaa atagacagat cgctgagata ggtgcctcac    5160
tgattaagca ttggtaactg tcagaccaag tttactcata tatactttag attgatttaa    5220
aacttcattt ttaatttaaa aggatctagg tgaagatcct ttttgataat ctcatgacca    5280
aaatccctta acgtgagttt tcgttccact gagcgtcaga ccccgtagaa aagatcaaag    5340
gatcttcttg agatcctttt tttctgcgcg taatctgctg cttgcaaaca aaaaaaccac    5400
cgctaccagc ggtggtttgt ttgccggatc aagagctacc aactctttt ccgaaggtaa    5460 ctggcttcag cagagcgcag ataccaaata ctgtccttct agtgtagccg tagttaggcc    5520
accacttcaa gaactctgta gcaccgccta catcctcgc tctgctaatc ctgttaccag    5580
tggctgctgc cagtggcgat aagtcgtgtc ttaccgggtt ggactcaaga cgatagttac    5640
cggataaggc gcagcggtcg ggctgaacgg ggggttcgtg cacacagccc agcttggagc    5700
gaacgaccta caccgaactg agatacctac agcgtgagca ttgagaaagc gccacgcttc    5760
ccgaagggag aaaggcggac aggtatccgg taagcggcag ggtcggaaca ggagagcgca    5820
cgagggagct ccagggggga aacgcctggt atctttatag tcctgtcggg tttcgccacc    5880
tctgacttga gcgtcgattt ttgtgatgct cgtcagggg gcggagccta tggaaaaacg    5940
ccagcaacgc ggcctttta cggttcctgg cctttgctg gccttttgct cacatgttct    6000
ttcctgcgtt atccctgat tctgtggata accgtattac cgcctttgag tgagctgata    6060
ccgctcgccg cagccgaacg accgagcgca gcgagtcagt gagcgaggaa gcggaagagc    6120
```

-continued

```
gcctgatgcg gtattttctc cttacgcatc tgtgcggtat ttcacaccgc agaccagccg    6180
cgtaacctgg caaaatcggt tacggttgag taataaatgg atgccctgcg taagcgggtg    6240
tgggcggaca ataaagtctt aaactgaaca aaatagatct aaactatgac aataaagtct    6300
taaactagac agaatagttg taaactgaaa tcagtccagt tatgctgtga aaaagcatac    6360
tggacttttg ttatggctaa agcaaactct tcattttctg aagtgcaaat tgcccgtcgt    6420
attaaagagg ggcgtggcca agggcatggt aaagactata ttcgcggcgt tgtgacaatt    6480
taccgaacaa ctccgcggcc gggaagccga tctcggcttg aacgaattgt taggtggcgg    6540
tacttgggtc gatatcaaag tgcatcactt cttcccgtat gcccaacttt gtatagagag    6600
ccactgcggg atcgtcaccg taatctgctt gcacgtagat cacataagca ccaagcgcgt    6660
tggcctcatg cttgaggaga ttgatgagcg cggtggcaat gccctgcctc cggtgctcgc    6720
cggagactgc gagatcatag atatagatct cactacgcgg ctgctcaaac ctgggcagaa    6780
cgtaagccgc gagagcgcca acaaccgctt cttggtcgaa ggcagcaagc gcgatgaatg    6840
tcttactacg gagcaagttc ccgaggtaat cggagtccgg ctgatgttgg gagtaggtgg    6900
ctacgtctcc gaactcacga ccgaaaagat caagagcagc ccgcatggat ttgacttggt    6960
cagggccgag cctacatgtg cgaatgatgc ccatacttga gccacctaac tttgttttag    7020
ggcgactgcc ctgctgcgta acatcgttgc tgctgcgtaa catcgttgct gctccataac    7080
atcaaacatc gacccacggc gtaacgcgct tgctgcttgg atgcccgagg catagactgt    7140
acaaaaaaac agtcataaca agccatgaaa accgccactg cgccgttacc accgctgcgt    7200
tcggtcaagg ttctggacca gttgcgtgag cgcatacgct acttgcatta cagtttacga    7260
accgaacagg cttatgtcaa ctgggttcgt gccttcatcc gtttccacgg tgtgcgtcac    7320
ccggcaacct tgggcagcag cgaagtcgag gcatttctgt cctggctggc gaacgagcgc    7380
aaggtttcgg tctccacgca tcgtcaggca ttggcggcct tgctgttctt ctacggcaag    7440
gtgctgtgca cggatctgcc ctggcttcag gagatcggaa gacctcggcc gtcgcggcgc    7500
ttgccggtgg tgctgacccc ggatgaagtg gttcgcatcc tcggttttct ggaaggcgag    7560
catcgtttgt tcgcccagga ctctagctat agttctagtg gttggctacg tatactccgg    7620
aatattaata gatcatggag ataattaaaa tgataaccat ctcgcaaata aataagtatt    7680
ttactgtttt cgtaacagtt ttgtaataaa aaaacctata aatattccgg attattcata    7740
ccgtcccacc atcgggcgc                                                 7759
```

<210> SEQ ID NO 8
<211> LENGTH: 7741
<212> TYPE: DNA
<213> ORGANISM: Artificial Sequence
<220> FEATURE:
<223> OTHER INFORMATION: pFastBac O_TUR_05_2009 VP2-S93F

<400> SEQUENCE: 8

```
ggatccggta accaaatatg ggggcgggtc aatcgtcacc agcaacgggg tctcagaatc      60
aaagcgggaa cacggggtct attatcaaca actactacat gcagcaatac caaaacagca     120
tggacaccca actgggcgac aacgctatct ctggcggttc aaacgagggc tcaactgaca     180
ccaccagcaa ccacacgacc aatacccaaa acaatgactg gttctctaag ctcgccagca     240
gcgctttcag cggcctgttc ggtgctcttc ttgcagacaa gaaaaccgag gaaactacgc     300
tgctggagga ccgtatcctg accactagga acggccacac gaccagcact acgcaaagca     360
gcgttggcgt gacctacggt tatgctacca ctgaagactt cgtttccggt cccaacacca     420
```

```
gcggcctgga gactcgtgtt gtgcaggctg aacgtttctt caagacccat ctgttcgact       480
gggttactag cgatagcttc ggacgttgcc acctgctgga gctgccaact gaccataaag       540
gagtgtacgg cttcctgacc gattcctacg cctatatgcg taacggctgg gacgtcgaag       600
taaccgctgt tggcaaccaa ttcaatggag ggtgcctact agttgctatg gtgcccgagc       660
tgtgtagcat caacaagcgt gaactgtacc aattaactct gttcccgcac cagttcatca       720
acccacgtac caatatgact gctcatatta ccgttccctt cgttggcgtg aaccgttacg       780
accaatataa ggtgcacaaa ccctggaccc tggttgttat ggttgtggcc ccctcaccg        840 tgaacactga aggcgctccc caaatcaagg tctacgcgaa cattgctccc accaacgtcc       900
atgtagccgg agagttcccc agcaaagaag gcatcttccc tgttgcttgc agcgacggat       960
acggcggtct ggtgacgacc gaccccaaga ccgctgaccc cgcatacggt aaagtttca      1020 accccctag gaacatgctg cccggacgtt tcactaactt ccttgacgtg gccgaggctt      1080
gccctacctt ccttcacttc gaaggcgatg tcccctacgt aactacgaag actgacagcg      1140
atcgtatcct cgctcaattc gaccttagcc tcgctgccaa acacatgagc aacaccttcc      1200
tggctggact tgcccaatac tatacccagt acagcggcac tatcaacctg catttcatgt      1260
tcaccggtcc cactgacgcg aaggctcgtt acatgatcgc ctatgcaccg cccggtatgg      1320 agcccccctaa aaccccgaa gctgctgctc actgcatcca tgctgagtgg acaccggcc       1380 tgaactctaa gttcactttc tcaattccct accttagcgc tgctgactac gcatataccg      1440
cttctgatac tgctgaaacc actaacgtcc aaggctgggt ttgtctgttc cagatcaccc      1500
acggaaaggc tgacggcgac gctctggttg tactagctag cgccggcaaa gacttcgagc      1560
tgcgcttacc cgttgacgct aggacccaaa cgaccagcgc tggcgaatca gctgaccccg      1620
tgaccgctac tgtcgagaac tacggagggg aaacccaagt ccagcgtcgt caacatactg      1680
acgtttcttt catcctggac cgtttcgtta aagtgacccc caaagaccaa atcaacgttc      1740
tggacctgat gcagacccca gctcacactc tggtgggcgc tctgttacgt accgctactt      1800
actatttcgc tgacctggag gtcgctgtaa agcatgaagg taatctgacc tgggttccca      1860
acggcgctcc cgagactgct ctggacaaca ctacgaatcc gaccgcttac cacaaggccc      1920
ctctgacccg tctcgcccta ccgtacactg ctccacatcg cgtgcttgcc accgcataca      1980
acggcaattg caagtacggt gaatctcaca ccactaacgt tcgtggagac ctgcaagtgc      2040
ttgctcagaa agcggctcgc accctgccca cttcattcaa ctacggcgcc atcaaggcaa      2100
cccgtgttac tgagctgctt tacaggatga aacgtgctga aacctactgt ccccgtcccc      2160
tcctagccat ccacccctca gaggctcgcc ataagcaaaa aattgttgct cctgtgaagc      2220
aattattaaa tttcgaccta ctgaagttag ctggggacgt tgaatcgaac ccgggaccca      2280
gcggccgcgg acctttttta gggaagatct ggccttccta caagggaagg ccagggaatt      2340
ttcttacgag ggacctgtga agaagcctgt cgctttgaaa gtgaaagcta agaacttgat      2400
tgtcactgag agtggagccc caccgaccga cttgcaaaag atggtcatgg caacaccaa       2460 gcctgttgag cttatcctcg acgggaagac ggtggccatt tgttgtgcta ccggagtgtt      2520
tggcactgcg tacctcgtgc ctcgtcatct ttttgcagaa aaatatgaca agatcatgct      2580
ggacggcaga gccatgacag acagtgacta cagagtgttt gaattcgaga ttaaagtaaa      2640
aggacaggac atgctctcag acgctgcgct catggtactc caccgtggga atcgcgtgag      2700
agacatcacg aaacactttc gtgacacagc aagaatgaag aaaggcaccc ctgttgtcgg      2760
```

-continued

```
agtgatcaac aatgccgacg ttgggagact gatcttctct ggtgaggcct taacctacaa    2820
ggacattgta gtgactatgg atggagacac catgcctggc ctgtttgcct acaaagccgc    2880
caccaaggct ggctactgtg ggggagccgt tcttgctaag gacggagctg acacattcat    2940
cgttggtacc cactccgcag gcggcaatgg agttggatac tgctcatgcg tctcgaggtc    3000
catgttgctg aaaatgaagg cgcacatcga ccccgaacca caccacgagt aatctagagg    3060
atcccctcag gaagcttgtc gagaagtact agaggatcat aatcagccat accacatttg    3120
tagaggtttt acttgcttta aaaaacctcc cacacctccc cctgaacctg aaacataaaa    3180
tgaatgcaat tgttgttgtt aacttgttta ttgcagctta taatggttac aaataaagca    3240
atagcatcac aaatttcaca aataaagcat ttttttcact gcattctagt tgtggtttgt    3300
ccaaactcat caatgtatct tatcatgtct ggatctgatc actgcttgag cctaggagat    3360
ccgaaccaga taagtgaaat ctagttccaa actattttgt cattttttaat tttcgtatta    3420 gcttacgacg ctacacccag ttcccatcta ttttgtcact cttccctaaa taatccttaa    3480
aaactccatt tccaccccctc ccagttccca actattttgt ccgcccacag cggggcattt    3540
ttcttcctgt tatgttttta atcaaacatc ctgccaactc catgtgacaa accgtcatct    3600
tcggctactt tttctctgtc acagaatgaa aatttttctg tcatctcttc gttattaatg    3660
tttgtaattg actgaatatc aacgcttatt tgcagcctga atggcgaatg gacgcgccct    3720
gtagcggcgc attaagcgcg gcgggtgtgg tggttacgcg cagcgtgacc gctacacttg    3780
ccagcgccct agcgcccgct cctttcgctt tcttcccttc ctttctcgcc acgttcgccg    3840
gctttccccg tcaagctcta aatcggggggc tccctttagg gttccgattt agtgctttac    3900
ggcacctcga ccccaaaaaa cttgattagg gtgatggttc acgtagtggg ccatcgccct    3960
gatagacggt ttttcgccct ttgacgttgg agtccacgtt ctttaatagt ggactcttgt    4020
tccaaactgg aacaacactc aaccctatct cggtctattc ttttgattta taagggattt    4080
tgccgatttc ggcctattgg ttaaaaaatg agctgattta acaaaaattt aacgcgaatt    4140
ttaacaaaat attaacgttt acaatttcag gtggcacttt tcggggaaat gtgcgcggaa    4200
cccctatttg tttatttttc taaatacatt caaatatgta tccgctcatg agacaataac    4260
cctgataaat gcttcaataa tattgaaaaa ggaagagtat gagtattcaa catttccgtg    4320
tcgcccttat tcccttttttt gcggcatttt gccttcctgt ttttgctcac ccagaaacgc    4380
tggtgaaagt aaaagatgct gaagatcagt tgggtgcacg agtgggttac atcgaactgg    4440
atctcaacag cggtaagatc cttgagagtt ttcgccccga agaacgtttt ccaatgatga    4500
gcacttttaa agttctgcta tgtggcgcgg tattatcccg tattgacgcc gggcaagagc    4560
aactcggtcg ccgcatacac tattctcaga atgacttggt tgagtactca ccagtcacag    4620
aaaagcatct tacggatggc atgacagtaa gagaattatg cagtgctgcc ataaccatga    4680
gtgataacac tgcggccaac ttacttctga caacgatcgg aggaccgaag gagctaaccg    4740
cttttttgca acatggggg gatcatgtaa ctcgccttga tcgttgggaa ccggagctga    4800
atgaagccat accaaacgac gagcgtgaca ccacgatgcc tgtagcaatg gcaacaacgt    4860
tgcgcaaact attaactggc gaactactta ctctagcttc ccggcaacaa ttaatagact    4920
ggatggaggc ggataaagtt gcaggaccac ttctgcgctc ggcccttccg gctggctggt    4980
ttattgctga taaatctgga gccggtgagc gtgggtctcg cggtatcatt gcagcactgg    5040
ggccagatgg taagccctcc cgtatcgtag ttatctacac gacggggagt caggcaacta    5100
tggatgaacg aaatagacag atcgctgaga taggtgcctc actgattaag cattggtaac    5160
```

-continued

```
tgtcagacca agtttactca tatatacttt agattgattt aaaacttcat ttttaattta    5220
aaaggatcta ggtgaagatc ctttttgata atctcatgac caaaatccct taacgtgagt    5280
tttcgttcca ctgagcgtca gaccccgtag aaaagatcaa aggatcttct tgagatcctt    5340
tttttctgcg cgtaatctgc tgcttgcaaa caaaaaaacc accgctacca gcggtggttt    5400
gtttgccgga tcaagagcta ccaactcttt ttccgaaggt aactggcttc agcagagcgc    5460
agataccaaa tactgtcctt ctagtgtagc cgtagttagg ccaccacttc aagaactctg    5520
tagcaccgcc tacatacctc gctctgctaa tcctgttacc agtggctgct gccagtggcg    5580
ataagtcgtg tcttaccggg ttggactcaa gacgatagtt accggataag cgcagcggt    5640 cgggctgaac ggggggttcg tgcacacagc ccagcttgga gcgaacgacc tacaccgaac    5700
tgagatacct acagcgtgag cattgagaaa gcgccacgct tcccgaaggg agaaaggcgg    5760
acaggtatcc ggtaagcggc agggtcggaa caggagagcg cacgagggag cttccagggg    5820
gaaacgcctg gtatctttat agtcctgtcg ggtttcgcca cctctgactt gagcgtcgat    5880
ttttgtgatg ctcgtcaggg gggcggagcc tatggaaaaa cgccagcaac gcggccttt    5940 tacggttcct ggccttttgc tggcctttt ctcacatgtt ctttcctgcg ttatcccctg    6000
attctgtgga taaccgtatt accgcctttg agtgagctga taccgctcgc cgcagccgaa    6060
cgaccgagcg cagcgagtca gtgagcgagg aagcggaaga cgcctgatg cggtattttc    6120 tccttacgca tctgtgcggt atttcacacc gcagaccagc cgcgtaacct ggcaaaatcg    6180
gttacggttg agtaataaat ggatgccctg cgtaagcggg tgtgggcgga caataaagtc    6240
ttaaactgaa caaaatagat ctaaactatg acaataaagt cttaaactag acagaatagt    6300
tgtaaactga aatcagtcca gttatgctgt gaaaaagcat actggacttt tgttatggct    6360
aaagcaaact cttcattttc tgaagtgcaa attgcccgtc gtattaaaga ggggcgtggc    6420
caagggcatg gtaaagacta tattcgcggc gttgtgacaa tttaccgaac aactccgcgg    6480
ccgggaagcc gatctcggct tgaacgaatt gttaggtggc ggtacttggg tcgatatcaa    6540
agtgcatcac ttcttcccgt atgcccaact ttgtatagag agccactgcg ggatcgtcac    6600
cgtaatctgc ttgcacgtag atcacataag caccaagcgc gttggcctca tgcttgagga    6660
gattgatgag cgcggtggca atgccctgcc tccggtgctc gccggagact gcgagatcat    6720
agatatagat ctcactacgc ggctgctcaa acctgggcag aacgtaagcc gcgagagcgc    6780
caacaaccgc ttcttggtcg aaggcagcaa gcgcgatgaa tgtcttacta cggagcaagt    6840
tcccgaggta atcggagtcc ggctgatgtt gggagtaggt ggctacgtct ccgaactcac    6900
gaccgaaaag atcaagagca gcccgcatgg atttgacttg gtcagggccg agcctacatg    6960
tgcgaatgat gcccatactt gagccaccta actttgtttt agggcgactg ccctgctgcg    7020
taacatcgtt gctgctgcgt aacatcgttg ctgctccata acatcaaaca tcgacccacg    7080
gcgtaacgcg cttgctgctt ggatgcccga ggcatagact gtacaaaaaa acagtcataa    7140
caagccatga aaaccgccac tgcgccgtta ccaccgctgc gttcggtcaa ggttctggac    7200
cagttgcgtg agcgcatacg ctacttgcat tacagtttac gaaccgaaca ggcttatgtc    7260
aactgggttc gtgccttcat ccgtttccac ggtgtgcgtc accggcaac cttgggcagc    7320 agcgaagtcg aggcatttct gtcctggctg gcgaacgagc gcaaggtttc ggtctccacg    7380
catcgtcagg cattggcggc cttgctgttc ttctacggca aggtgctgtg cacggatctg    7440
ccctggcttc aggagatcgg aagacctcgg ccgtcgcggc gcttgccggt ggtgctgacc    7500
```

-continued

```
ccggatgaag tggttcgcat cctcggtttt ctggaaggcg agcatcgttt gttcgcccag          7560
gactctagct atagttctag tggttggcta cgtatactcc ggaatattaa tagatcatgg          7620
agataattaa aatgataacc atctcgcaaa taaataagta ttttactgtt ttcgtaacag          7680
ttttgtaata aaaaaaccta taaatattcc ggattattca taccgtccca ccatcgggcg          7740
c                                                                          7741

<210> SEQ ID NO 9
<211> LENGTH: 7744
<212> TYPE: DNA
<213> ORGANISM: Artificial Sequence
<220> FEATURE:
<223> OTHER INFORMATION: pFastBac A_IRN_7_13 VP2-H93F

<400> SEQUENCE: 9
ggatccggta accaaatatg ggagcgggac aatcgtcgcc tgccacgggg agccaaaacc            60
aatctgggaa cactggaagc atcatcaata actactatat gcaacaatac caaaacagca          120
tggacaccca actgggcgac aacgctatca gcggcggttc taacgaggga tctaccgaca          180
ccacttcaac tcacacgacc aacacccaaa acaatgactg gttcagcaag ctcgctagct          240
ctgccttcag cggcctgttc ggcgctctgc ttgcggacaa gaaaaccgag gaaactacgc          300
tgctggagga ccgtatcctc accactcgca acggccacac gaccagcact acgcaaagca          360
gcgtcggagt aacttacggg tattctaccg agaagaccga tgtttcggga ccaaacacca          420
gcggcctgga gacccgtgtt gtgcaggctg aacgtttctt caagaaacac ctgttcgact          480
ggaccactga taaggctttc ggccatcttg agaaacttga actccccacc gagcacaagg          540
gagtttacgg gttcctggtg gactctttcg cttacatgcg taacggctgg gacgtcgaag          600
tgaccgccgt tggcaaccaa ttcaatggag ggtgcctact agttgctatg gtgcccgagt          660
ggaaggagtt cacgacccgt gaaaaatacc aactaacctt attcccgcac cagttcatca          720
accctcgtac caatatgact gctcatatta ccgttcccta ccttggcgtt aaccgttacg          780
accaatataa gcagcacaaa ccctggaccc tggttgttat ggttgtgagc cctcttacta          840
ccagcaacat cggcgcttca caaatcaagg tttacgctaa catcgccccc accttcgtcc          900
atgtagctgg cgagctgccc tcaaaagaag gaatcgttcc agtggcttgc agcgacggat          960
acggcggtct ggttactact gaccccaaga cagctgaccc cgtctacggc atggtatata         1020 accccccctcg tactaattac cccggtcgct tcaccaacct tctcgacgtg gctgaggctt         1080
gccccacctt cctgtgtttc gacggaggca agccctacgt tgaaaccagg actgacgctc         1140
aacgtctatt agccaagttc gatgtgtcac tcgctgccaa acacatgtcg aacacctacc         1200
tgagcggaat cgctcaatac tatactcagt acagcggcac catcaacctt catttcatgt         1260
tcaccggttc aactgactcg aaggcacgtt acatggttgc ctatatcccg ccaggaatgg         1320 acacccccccc tgatactcct gagaaggcag cgcactgcat ccatgctgaa tgggacactg         1380
gtctcaactc taaattcacc ttctcaatcc cctacgttag cgctgccgac tacgcatata         1440
ctgccagcga tgaggcagaa gcgaccaacg ttcaaggatg ggtgtgtatc taccaaatta         1500
ctcacggcaa ggctgagcaa gacacccctgg ttgttagcgc cagcgctggc aaggacttcg         1560
aactgaggct tcccatcgat ccccgtgctc aaacgactac tgcaggagag tcagccgacc         1620
ccgtcactac cactgttgag aactacggcg tgaaactca agttcagcgt cgtcaccata         1680
ccgacgtggg attcatcatg gatcgtttcg tgaagatcag cccggtcggc ccaactcacg         1740
tgatcgacct catgcaaacc caccaacacg ctctggttgg cgctctgctt cgtgctgcga        1800
```

```
cctactattt cagcgacctt gagatcgttg tgcgtcacga aggtcatctc acctgggtgc      1860
ccaacggcgc tcccgtgggc gctctggtta acacctctaa tcctactgct tactgcaagg      1920
agcccttcac tcgtctcgct ctaccgtaca ccgccccaca ccgcgttctt gctaccgtgt      1980
acaacggcgt tagcaaatac agcaccactg gaggcgacag gcgtggcgac ctgggtagcc      2040
ttgctgcccg tgttgcagcg caccttccca gcagcttcaa cttcggcgcc atcaaggcaa      2100
ccaacattca tgagctgctg gttcgtatga aaagggctga actctactgt ccccgtccct      2160
tactggccgt cgaggttagc agccaagacc gccacaagca gaaaatcatt gcacccgcga      2220
agcaattact gaacttcgac ctactgaaat tagcgggaga cgttgaatcg aaccccggac      2280
ccagcggccg cggacctttt ttagggaaga tctggccttc ctacaaggga aggccaggga      2340
attttcttac gagggacctg tgaagaagcc tgtcgctttg aaagtgaaag ctaagaactt      2400
gattgtcact gagagtggag ccccaccgac cgacttgcaa aagatggtca tgggcaacac      2460
caagcctgtt gagcttatcc tcgacgggaa gacggtggcc atttgttgtg ctaccggagt      2520
gtttggcact gcgtacctcg tgcctcgtca tcttttttgca gaaaaatatg acaagatcat      2580
gctggacggc agagccatga cagacagtga ctacagagtg tttgaattcg agattaaagt      2640
aaaaggacag gacatgctct cagacgctgc gctcatggta ctccaccgtg ggaatcgcgt      2700
gagagacatc acgaaacact ttcgtgacac agcaagaatg aagaaaggca cccctgttgt      2760
cggagtgatc aacaatgccg acgttgggag actgatcttc tctggtgagg ccttaacctta      2820 caaggacatt gtagtgacta tggatggaga caccatgcct ggcctgtttg cctacaaagc      2880
cgccaccaag gctggctact gtgggggagc cgttcttgct aaggacggag ctgacacatt      2940
catcgttggt acccactccg caggcggcaa tggagttgga tactgctcat gcgtctcgag      3000
gtccatgttg ctgaaaatga aggcgcacat cgaccccgaa ccacaccacg agtaatctag      3060
aggatcccct caggaagctt gtcgagaagt actagaggat cataatcagc cataccacat      3120
ttgtagaggt tttacttgct ttaaaaaacc tcccacacct cccctgaac ctgaaacata      3180 aaatgaatgc aattgttgtt gttaacttgt ttattgcagc ttataatggt tacaaataaa      3240
gcaatagcat cacaaatttc acaaataaag cattttttc actgcattct agttgtggtt      3300
tgtccaaact catcaatgta tcttatcatg tctggatctg atcactgctt gagcctagga      3360
gatccgaacc agataagtga aatctagttc caaactattt tgtcattttt aattttcgta      3420
ttagcttacg acgctacacc cagttcccat ctattttgtc actcttccct aaataatcct      3480
taaaaactcc atttccaccc ctcccagttc ccaactattt tgtccgccca cagcggggca      3540
tttttcttcc tgttatgttt ttaatcaaac atcctgccaa ctccatgtga caaaccgtca      3600
tcttcggcta cttttttctct gtcacagaat gaaaattttt ctgtcatctc ttcgttatta      3660
atgtttgtaa ttgactgaat atcaacgctt atttgcagcc tgaatggcga atggacgcgc      3720
cctgtagcgg cgcattaagc gcggcgggtg tggtggttac gcgcagcgtg accgctacac      3780
ttgccagcgc cctagcgccc gctcctttcg ctttcttccc ttcctttctc gccacgttcg      3840
ccggctttcc ccgtcaagct ctaaatcggg ggctcccttt agggttccga tttagtgctt      3900
tacggcacct cgaccccaaa aaacttgatt agggtgatgg ttcacgtagt gggccatcgc      3960
cctgatagac ggtttttcgc cctttgacgt tggagtccac gttctttaat agtggactct      4020
tgttccaaac tggaacaaca ctcaaccta tctcggtcta ttcttttgat ttataaggga      4080
ttttgccgat ttcggcctat tggttaaaaa atgagctgat ttaacaaaaa tttaacgcga      4140
```

-continued

```
attttaacaa aatattaacg tttacaattt caggtggcac ttttcgggga aatgtgcgcg        4200
gaacccctat ttgtttattt ttctaaatac attcaaatat gtatccgctc atgagacaat        4260
aaccctgata aatgcttcaa taatattgaa aaaggaagag tatgagtatt caacatttcc        4320
gtgtcgccct tattcccttt tttgcggcat tttgccttcc tgtttttgct cacccagaaa        4380
cgctggtgaa agtaaaagat gctgaagatc agttgggtgc acgagtgggt tacatcgaac        4440
tggatctcaa cagcggtaag atccttgaga gttttcgccc cgaagaacgt tttccaatga        4500
tgagcacttt taaagttctg ctatgtggcg cggtattatc ccgtattgac gccgggcaag        4560
agcaactcgg tcgccgcata cactattctc agaatgactt ggttgagtac tcaccagtca        4620
cagaaaagca tcttacggat ggcatgacag taagagaatt atgcagtgct gccataacca        4680
tgagtgataa cactgcggcc aacttacttc tgacaacgat cggaggaccg aaggagctaa        4740
ccgctttttt gcacaacatg ggggatcatg taactcgcct tgatcgttgg gaaccggagc        4800
tgaatgaagc cataccaaac gacgagcgtg acaccacgat gcctgtagca atggcaacaa        4860
cgttgcgcaa actattaact ggcgaactac ttactctagc ttcccggcaa caattaatag        4920
actggatgga ggcggataaa gttgcaggac cacttctgcg ctcggccctt ccggctggct        4980
ggtttattgc tgataaatct ggagccggtg agcgtgggtc tcgcggtatc attgcagcac        5040
tggggccaga tggtaagccc tcccgtatcg tagttatcta cacgacgggg agtcaggcaa        5100
ctatggatga acgaaataga cagatcgctg agataggtgc ctcactgatt aagcattggt        5160
aactgtcaga ccaagtttac tcatatatac tttagattga tttaaaactt catttttaat        5220
ttaaaaggat ctaggtgaag atcctttttg ataatctcat gaccaaaatc ccttaacgtg        5280
agttttcgtt ccactgagcg tcagaccccg tagaaaagat caaaggatct tcttgagatc        5340 cttttttttct gcgcgtaatc tgctgcttgc aaacaaaaaa accaccgcta ccagcggtgg        5400
tttgtttgcc ggatcaagag ctaccaactc tttttccgaa ggtaactggc ttcagcagag        5460
cgcagatacc aaatactgtc cttctagtgt agccgtagtt aggccaccac ttcaagaact        5520
ctgtagcacc gcctacatac ctcgctctgc taatcctgtt accagtggct gctgccagtg        5580
gcgataagtc gtgtcttacc gggttggact caagacgata gttaccggat aaggcgcagc        5640
ggtcgggctg aacggggggt tcgtgcacac agcccagctt ggagcgaacg acctacaccg        5700
aactgagata cctacagcgt gagcattgag aaagcgccac gcttcccgaa gggagaaagg        5760
cggacaggta tccggtaagc ggcagggtcg aacaggaga gcgcacgagg gagcttccag        5820
ggggaaacgc ctggtatctt tatagtcctg tcgggtttcg ccacctctga cttgagcgtc        5880
gatttttgtg atgctcgtca gggggggcgga gcctatggaa aaacgccagc aacgcggcct        5940
ttttacggtt cctggccttt tgctggcctt ttgctcacat gttctttcct gcgttatccc        6000
ctgattctgt ggataaccgt attaccgcct ttgagtgagc tgataccgct cgccgcagcc        6060
gaacgaccga gcgcagcgag tcagtgagcg aggaagcgga agagcgcctg atgcggtatt        6120
ttctccttac gcatctgtgc ggtatttcac accgcagacc agccgcgtaa cctggcaaaa        6180
tcggttacgg ttgagtaata aatggatgcc ctgcgtaagc gggtgtgggc ggacaataaa        6240
gtcttaaact gaacaaaata gatctaaact atgacaataa agtcttaaac tagacagaat        6300
agttgtaaac tgaaatcagt ccagttatgc tgtgaaaaag catactggac ttttgttatg        6360
```

-continued

```
gctaaagcaa actcttcatt ttctgaagtg caaattgccc gtcgtattaa agaggggcgt   6420
ggccaagggc atggtaaaga ctatattcgc ggcgttgtga caatttaccg aacaactccg   6480
cggccgggaa gccgatctcg gcttgaacga attgttaggt ggcggtactt gggtcgatat   6540
caaagtgcat cacttcttcc cgtatgccca actttgtata gagagccact gcgggatcgt   6600
caccgtaatc tgcttgcacg tagatcacat aagcaccaag cgcgttggcc tcatgcttga   6660
ggagattgat gagcgcggtg gcaatgccct gcctccggtg ctcgccggag actgcgagat   6720
catagatata gatctcacta cgcggctgct caaacctggg cagaacgtaa gccgcgagag   6780
cgccaacaac cgcttcttgg tcgaaggcag caagcgcgat gaatgtctta ctacggagca   6840
agttcccgag gtaatcggag tccggctgat gttgggagta ggtggctacg tctccgaact   6900
cacgaccgaa aagatcaaga gcagcccgca tggatttgac ttggtcaggg ccgagcctac   6960
atgtgcgaat gatgcccata cttgagccac ctaactttgt tttagggcga ctgccctgct   7020
gcgtaacatc gttgctgctg cgtaacatcg ttgctgctcc ataacatcaa acatcgaccc   7080
acggcgtaac gcgcttgctg cttggatgcc cgaggcatag actgtacaaa aaaacagtca   7140
taacaagcca tgaaaaccgc cactgcgccg ttaccaccgc tgcgttcggt caaggttctg   7200
gaccagttgc gtgagcgcat acgctacttg cattacagtt tacgaaccga acaggcttat   7260
gtcaactggg ttcgtgcctt catccgtttc cacggtgtgc gtcacccggc aaccttgggc   7320
agcagcgaag tcgaggcatt tctgtcctgg ctggcgaacg agcgcaaggt ttcggtctcc   7380
acgcatcgtc aggcattggc ggccttgctg ttcttctacg gcaaggtgct gtgcacggat   7440
ctgccctggc ttcaggagat cggaagacct cggccgtcgc ggcgcttgcc ggtggtgctg   7500
accccggatg aagtggttcg catcctcggt tttctggaag gcgagcatcg tttgttcgcc   7560
caggactcta gctatagttc tagtggttgg ctacgtatac tccggaatat taatagatca   7620
tggagataat taaaatgata accatctcgc aaataaataa gtattttact gttttcgtaa   7680
cagttttgta ataaaaaaac ctataaatat tccggattat tcataccgtc ccaccatcgg   7740
gcgc                                                                 7744
```